United States Patent [19]

Beecher et al.

[11] Patent Number: 5,192,984
[45] Date of Patent: Mar. 9, 1993

[54] APPARATUS AND METHOD FOR DETERMINATION OF CONCENTRATIONS

[75] Inventors: Gary R. Beecher, Laurel; David L. Kemper, Silver Spring; John E. Jordan, Germantown, all of Md.

[73] Assignee: Environmental Analytical Systems, Inc., Elkridge, Md.

[21] Appl. No.: 630,087

[22] Filed: Dec. 19, 1990

[51] Int. Cl.[5] .................................................. G01N 21/01
[52] U.S. Cl. ................................... 356/433; 356/410; 356/427; 356/246; 250/576
[58] Field of Search ................ 356/433, 432, 436, 73, 356/244, 246, 410, 427, 426; 250/573, 576

[56] References Cited

U.S. PATENT DOCUMENTS 4,013,413  3/1977  Stewart et al. .................... 23/230 R

OTHER PUBLICATIONS

Automated Titrations: the Use of Automated Multiple Flow Injection Analysis for the Titration of Discrete Samples, Kent K. Stewart, et al., Journal of Automated Chemistry, vol. 3, pp. 30–32 (1981).
Exponential Dilution Chambers for Scale Expansion in Flow Injection Analysis, Kent K. Stewart, et al., Analytical Chemistry, vol. 54, No. 13, pp. 2368–2372 (1982).

Primary Examiner—Vincent P. McGraw
Assistant Examiner—LaCharles Keesee
Attorney, Agent, or Firm—Michael W. York

[57] ABSTRACT

Apparatus and method for determination of concentrations of a substance in solution in a sample by determining the time between when the substance first appears and when it disappears. The time between the appearance and the disappearance of the substance is used to determine the concentrations of the substance in a sample. The apparatus includes many elements of a flow injection analysis system but also includes a very important stirred dilution chamber that enables the apparatus to use a simplified detection system that is capable of being used over a wide range of sample concentrations. The apparatus can include a microwave digestion system and in one embodiment a continuous flow microwave digestion system.

9 Claims, 10 Drawing Sheets

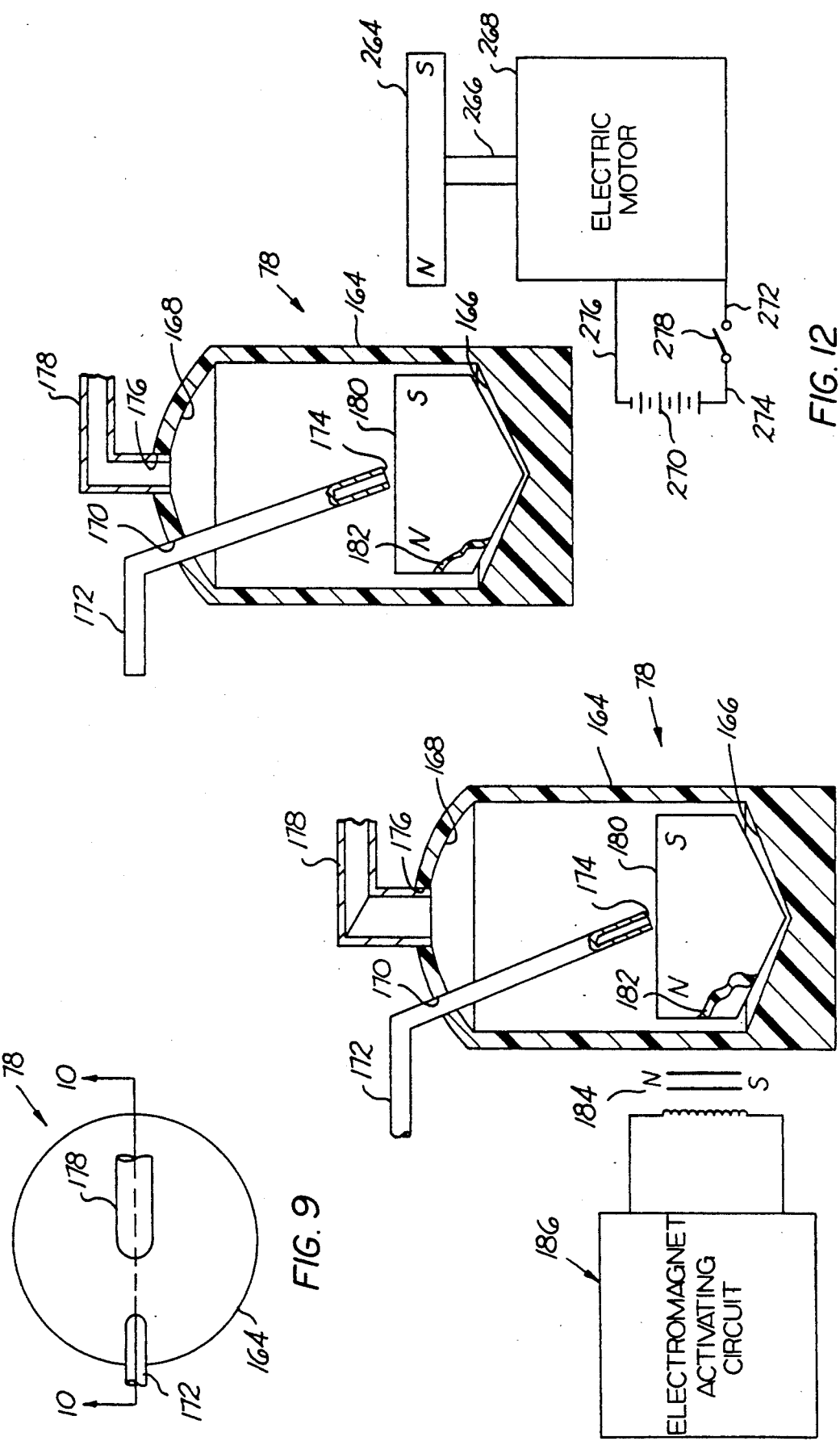

APPARATUS AND METHOD FOR DETERMINATION OF CONCENTRATIONS

BACKGROUND OF THE INVENTION

There have been numerous apparatus and methods for the determination of concentrations in samples in the past. Methods which employ reactions to form colored complexes and analysis of molecules which have an inherent ability to absorb light are governed by Beer's Law. Beer's Law states that at a specified wavelength of light the concentration of an analyte is directly proportional to the amount of light energy absorbed at a constant path length of light. The extent of light absorption and subsequently the analyte concentration is calculated from data generated by an electro-optical device called a colorimeter.

A colorimeter employs a light source, a method for selecting specific light energy, a device with a fixed optical path length for retention of the colored complex or molecules to be quantified and a detection system. The detection system consists of a device to measure light intensity and appropriate electronic circuitry to prevent the results in the desired format. The more precise the measurement required for calculating the concentration, the more sophisticated the design of the colorimeter must be. Most often data are presented as absorbance which is calculated by taking the logarithm (base 10) of the quantity, intensity of light incident to the sample divided by intensity of light transmitted through the sample.

When the absorption of light energy by a sample is large, which is the case with a high concentration of analyte, a reliable value cannot be determined because the detected signal is outside of the operating range of the colorimeter. In this case, the chemistry of the analysis may continue to obey Beer's Law, but instrument limitations prevent the accurate measurement of the maximum light absorption. For accurate analysis, the sample must be diluted, remeasured and the operator must mathematically compensate for the dilution during the calculation of analyte concentration.

Measurement in a colorimeter where the samples are in a flowing stream generates a continuum of absorbance data with respect to time. The response of the system to a sample is a smooth "peak" where the response moves away from a "baseline" or constant light absorption, goes through a maximum and subsequently returns to baseline after the sample has passed through the colorimeter. The gradation of absorbance in a peak is created by dilution occurring at the interface between the sample and the carrier in the flowing stream. The shape of the peak remains constant for a given system, but peak height and area of the peak change proportionally to concentration of analyte in a sample.

Traditional methods of calculating concentration are based on peak height or peak area used in a ratiometric relationship given by the equation:

Concentration of unknown = Concentration of standard/Peak area (height) of standard × Peak area (height) of unknown.

Both area and peak height measurements require that the method of detection always accurately measure the highest absorbance; that the detection circuitry be linear in response; and that a high enough signal to noise ratio be present to measure very low concentrations. The restraint for these parameters prevents the accurate measurement of analyte concentration over wide ranges and requires that dilution of samples which have concentrations of the analyte which absorb outside of the dynamic range of the detection system be carried out prior to analysis. This nullifies many of the advantages of automated instrumentation. In spite of this, peak area and peak height are the commonly used measurements for calculating the concentration of an analyte in colorimetric chemistry.

A third parameter, peak width is also mathematically correct for calculating concentration (peak area is proportional to peak height X peak width) and in theory could be used, but in practice this has not been possible by direct measurement. The difficulty with this approach is the imprecision of measuring the width of a normally generated peak due to the asymptotic nature of the curve at the baseline.

This invention overcomes previous problems associated with apparatus and methods for determining analyte concentrations in solutions. No longer is a very sophisticated colorimeter required. The invention does not need to be concerned with linearity of electronic response to changes in light energy and low signal to noise ratios at low light levels. Moreover, the invention is accurate over a wide range of concentrations including very high sample concentrations when normally a reliable value could not be determined since the detected signal would be outside the operating range of the colorimeter.

The invention uses the general principles of flow injection analysis (FIA). However, a stirred dilution chamber is introduced into the system which significantly alters the operation and performance of the system. When such a device is introduced into an FIA system, the time sample concentration profile observed at the detector is modified considerably compared to normally generated peak shapes. As the sample, that is confined to a small volume relative to the volume of the stirred dilution chamber, first enters the chamber, the concentration of analyte in the chamber increases dramatically. Subsequently, the level of analyte goes through a maximum concentration and then decreases following an exponential function created by the continuous dilution of sample by addition of newly entering reagent. Of significance to this invention is that as concentration of analyte in the sample increases, the time required to "clear" the sample from the dilution chamber also increases. In this case, time is proportional to the logarithm of the sample concentration.

The advantage of such a device and relationship in an analytical system is that only time from appearance to disappearance of the sample at the detector needs to be measured. Concentrations of analyte in unknown samples can then be calculated from standard curves which establish the time sample concentration relationship represented by the following equation:

Logarithm concentration of unknown = [(Logarithm concentration of standard)/Peak width of standard] × Peak width of unknown.

This relationship has been proven to hold true for concentrations over ranges of concentration not possible in conventional colorimetric, phosphorescent or fluorescent methods.

Now, since only the appearance or disappearance of analyte exiting from the dilution chamber must be detected, for those analytes with inherent light absorption characteristics or which are coupled to a colored, phosphorescent or fluorescent indicator, a simplified detector can be used. This detector can comprise an appropriate light emitting diode (LED), a flow cell or section of instrument tubing through which the colored analyte is observed, a photosensitive diode detector and associated electronics. In operation, the electrical signal from the output of the photodiode is monitored. As the colored analyte appears in the flow cell between the LED and photodiode detector the intensity of the electrical signal changes. This signal continues to change until the analyte and sample have cleared the dilution chamber and detector. At a predetermined level above the baseline as measured by the photodiode detector (trigger level) a timer is started. The timer is stopped when the signal from the photodiode detector returns to the trigger level. The resulting measured time is proportional to the concentration of analyte in the sample. As a result, wide ranges of concentrations of analyte in unknown samples can be determined without regard to previous instrumental problems which limited the accurate measure of parameters from which concentrations are calculated.

This invention is applicable to any analyte which absorbs light or that can be associated with a colored complex. Examples of such analytes include ammonia, hydrogen ions, phosphate, a large number of inorganic ions including nickel, thallium, iron and many other inorganic and organic compounds important in society and commerce. In addition, analytes that are fluorescent or luminescent or that can be coupled to a fluorescent or luminescent molecule can also be analyzed with this invention. In this case the detector must be changed to measure the appearance and disappearance of fluorescence or luminescence rather than color. In addition, analytes that emit nuclear radiation can also be measured.

SUMMARY OF THE INVENTION

This invention related to apparatus and methods for determination of concentrations and more particularly to apparatus and methods in which a sample whose concentration is to be measured is injected into a carrier stream.

Accordingly, it is an object of the invention to provide an apparatus and method for the determination of concentrations that are useful with concentration determinations where a sample is injected into a carrier stream.

It is also an object of the invention to provide an apparatus and method for the determination of concentrations that are used in connection with the principles of flow injection analysis.

It is an object of the invention to provide an apparatus and method for the determination of concentrations that permit samples to be analyzed with a high degree of precision.

It is an object of the invention to provide an apparatus and method for the determination of concentrations that can be used with samples containing wide ranges of concentrations of substances.

It is an object of the invention to provide an apparatus and method for the determination of concentrations that do not require a sophisticated detection system.

It is an object of the invention to provide an apparatus and method for the determination of concentrations that are well suited for use with samples having high concentrations of a substance.

It is an object of the invention to provide an apparatus and method for the determination of concentrations that do not require additional dilution of samples with high concentrations to enable them to be properly measured.

It is an object of the invention to provide an apparatus and method for the determination of concentrations that do not require the determination of peak height in connection with concentration of a substance versus time.

It is also an object of the invention to provide an apparatus and method for the determination of concentrations that do not require the determination of peak area in connection with the concentration of a substance versus time.

It is an object of the invention to provide an apparatus and method for the determination of concentrations that do not require a high signal to noise ratio at low concentrations of a substance.

It is an object of the invention to provide an apparatus and method for the determination of concentrations that are tolerant of light source fluctuations when concentrations of substances are being measured.

It is an object of the invention to provide an apparatus and method for the determination of concentrations that do not require a linear response of light energy proportional to concentration when concentrations of substances are being determined.

It is an object of the invention to provide an apparatus and method for the determination of concentrations that require less complex equipment than in the past.

It is an object of the invention to provide an apparatus and method for the determination of concentrations that require less expensive equipment than in the past.

It is an object of the invention to provide an apparatus and method for the determination of concentrations that have increased reliability.

It is an object of the invention to provide an apparatus and method for the simplified determination of concentrations.

It is an object of the invention to provide an apparatus and method for the determination of concentrations that permit more rapid analysis of samples.

It is an object of the invention to provide an apparatus and method for the determination of concentrations that require less equipment set up time.

It is an object of the invention to provide an apparatus and method for the determination of concentrations that require less equipment maintenance.

It is an object of the invention to provide an apparatus and method for the determination of concentrations that require less operator or user training.

These and other objects of the invention will become apparent from the following description of the invention of apparatus for determination of concentrations of a substance in a system that includes a sample flow system, a reaction flow system for reacting with samples from said sample flow system, means for introducing samples from said sample flow system into said reaction flow system and means for rapidly and continuously diluting the substance whose concentration is to be determined. The previous objects and others will also become apparent from the invention of a method for determining the concentration of a substance in a sample that includes the steps of providing a sample containing an unknown amount of a substance, providing a volume of carrier fluid, injecting the sample into the volume of carrier fluid, continuously diluting the sample with carrier fluid, detecting the initial presence of the substance in the carrier fluid through the use of the detector, detecting the subsequent lack of presence of the substance in the carrier fluid through the use of the detector, and determining the elapsed time from the detection of the initial presence of the substance through the use of the detector and the detection of the subsequent lack of presence of the substance through the use of the detector.

BRIEF DESCRIPTION OF THE DRAWINGS

The invention will be hereinafter described in considerable detail with reference to the appended drawings in which:

FIG. 9 is a top plan view of a dilution chamber that forms part of the present invention;

FIG. 10 is a sectional view of the dilution chamber that forms part of the present invention taken substantially on the line 10—10 of FIG. 7 and an associated electromagnet and electromagnet activating circuit;

FIG. 12 is a view of the dilution chamber of FIG. 10 in section combined with a side elevational view of a magnet and magnet driving motor that form an alternative embodiment to the structure set forth in FIG. 10;

DETAILED DESCRIPTION OF THE PREFERRED EMBODIMENTS

Figure 1:
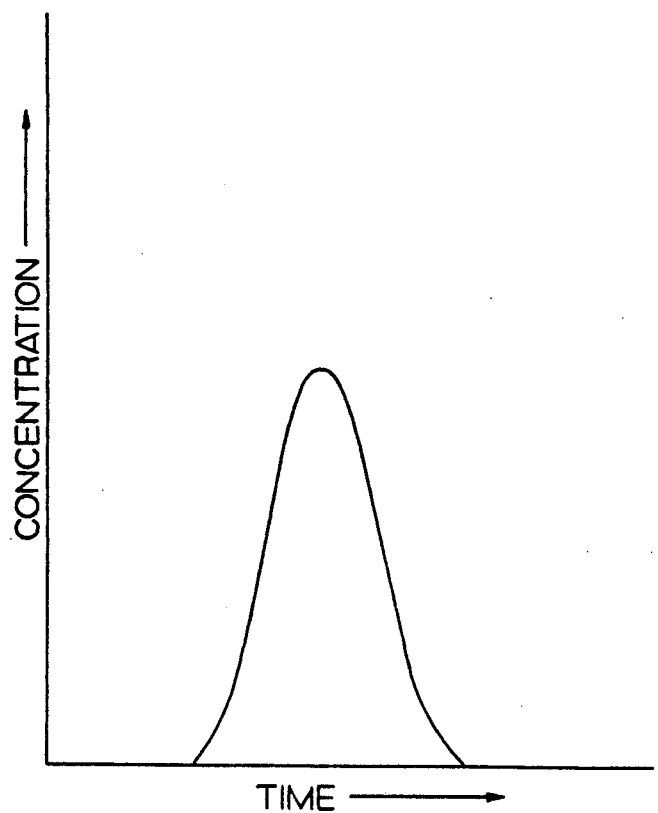
FIG. 1 is a graph of concentration versus time associated with prior art apparatus for determination of concentrations.

FIG. 1 illustrates a typical graph of concentration of a substance versus time that is seen by the detector in a prior art flow injection analysis apparatus. With such prior art apparatus which provides the values of concentration of sample versus time it is necessary to determine maximum peak height or the peak area to obtain a resulting value for the concentration of a substance in a sample that is being analyzed.

The measurement of both the peak height and of the area under the curve both require that the detector that is being used always detect the highest concentration. In addition, the light source cannot have fluctuations in energy levels, the detection circuitry must be linear in its response and there also must be a high enough signal to noise ratio at very low concentrations to obtain accurate measurements. These requirements for peak height and area measurements prevent the accurate measurement of concentrations over wide ranges.

Figure 2:
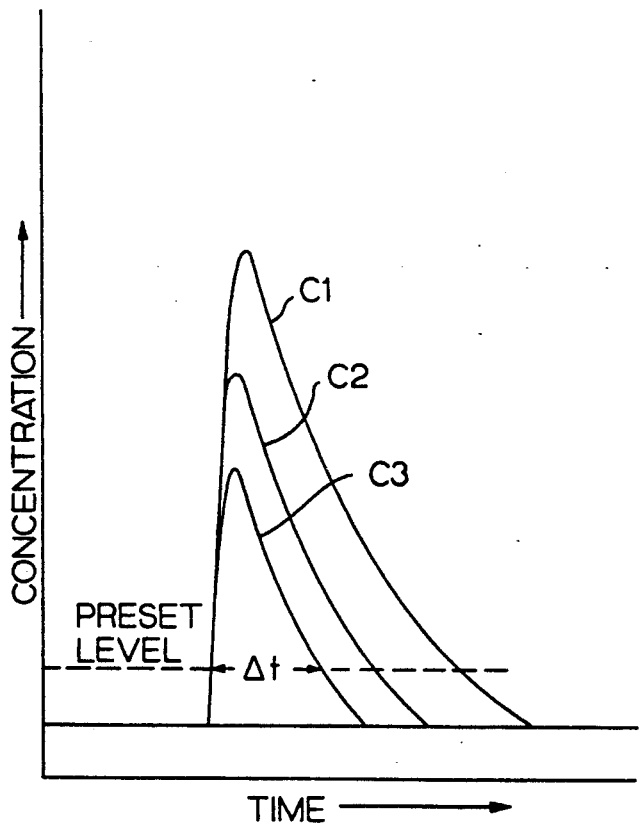
FIG. 2 is a graph of concentration versus time obtained with the apparatus and method for determination of concentrations of the present invention.

However, with this invention a different approach is used as illustrated in FIG. 2. FIG. 2 illustrates graphs of concentrations of a substance versus time when a sample is injected into a dilution chamber that forms part of the invention. As illustrated in FIG. 2, when the sample is injected into the dilution chamber, the concentration increases rapidly. Subsequently, the concentration reaches its maximum and then the concentration decreases in an exponential manner. Also, as illustrated, the time for the substance to leave the dilution chamber increases with an increase in the concentration as illustrated by the various curves labeled C3, C2, and C1 that represent samples with increasing concentrations of a substance.

Since, as illustrated in FIG. 2, the time of disappearance of the substance is related to its concentration with the dilution chamber, only the appearance and the subsequent disappearance of the substance need be detected to obtain time information that can then be converted to concentration (as illustrated by t). This allows a simplified detector to be used and it also allows the measurement of samples having a wide range of concentrations.

Figure 3:
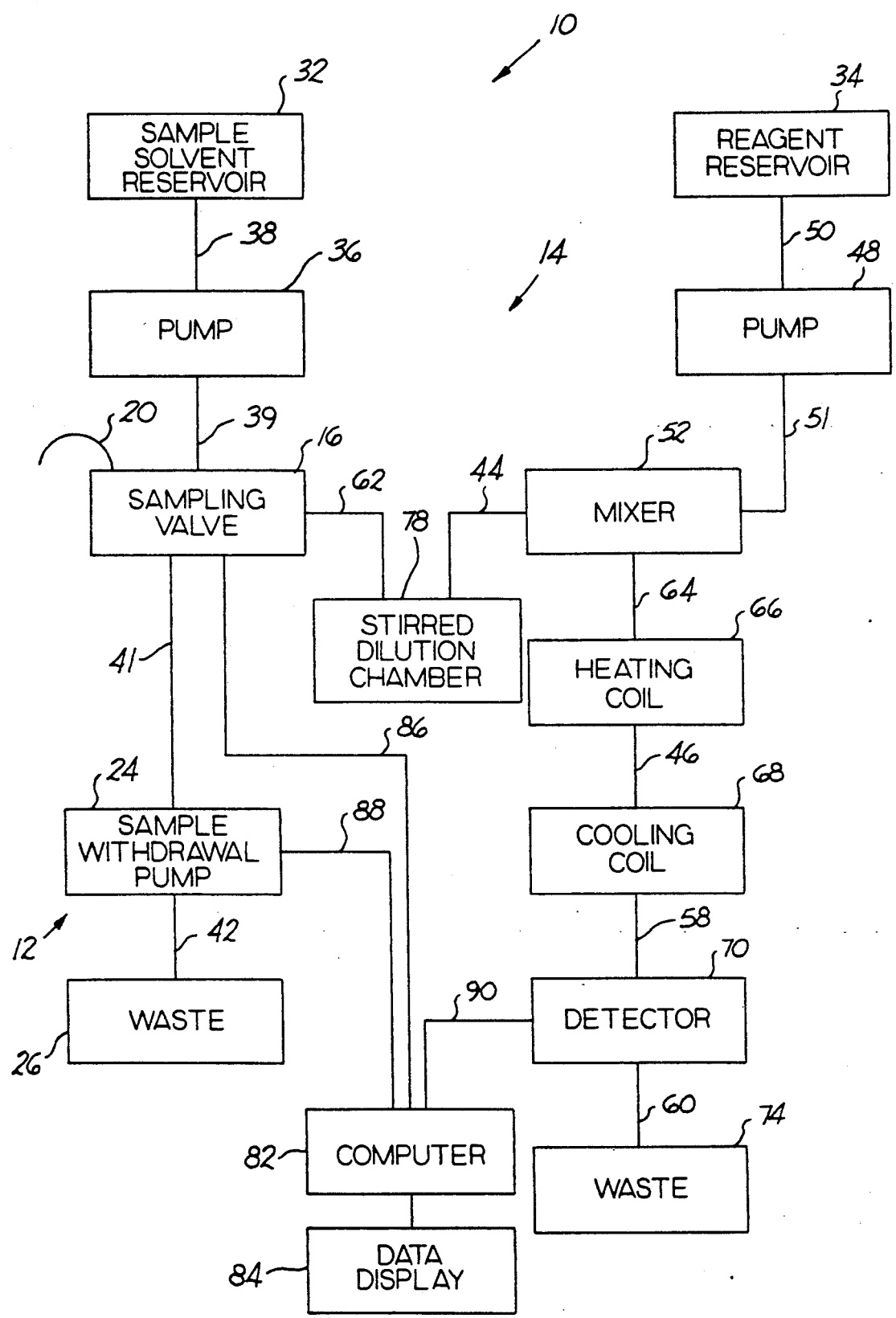
FIG. 3 is a block diagram of the one embodiment of apparatus for determination of concentration of the present invention.

The apparatus for determination of concentrations invention is schematically represented in block diagram form in FIG. 3 and is designated generally by the number 10. The apparatus for the determination of concentrations 10 comprises two separate systems, the sample flow system 12 and the reaction flow system 14, connected by one element common to both systems, the stream sampling valve 16.

Sample flow system 12 is provided with a sample probe 20, withdrawal pump 24 and a waste tank 26. The sample probe 20 can be used in conjunction with a continuously flowing stream of sample, a single sample reservoir or a sample holder (not shown) which can comprise a circular or rotary plate having provision for holding a plurality of sample cups or tubes as illustrated and described in U.S. Pat. No. 4,013,413 that is incorporated herein by reference. In the case of a sample holder the sample probe 20 is operated by any commercially available suitable mechanism to withdraw a sample, in alternating sequence, a portion of sample from a sample tube or the like (not shown) that is in take-off position at that moment, then a portion of wash solution from a reservoir (not shown), then a portion of the sample in the next succeeding tube (not shown), and so forth until all of the samples have been analyzed. Since the pump 24 operates continuously during sampling, air is drawn into probe 20 during the time that the probe moves from sample to wash solution and again when it moves back to the next sample. Consequently, samples and wash solution are separated from each other by a segment of air. More specifically, successive samples are separated from each other by individual segments of air, wash solution and air. Sample flow system 12 and more specifically probe 20 is connected to stream sampling valve 16 through which samples, wash solutions and air segments are conducted and also through which wash solutions, air segments, and portions of samples not removed from sample flow system 12 by stream sampling valve 16 are withdrawn through the conduit 41, through the pump 24 and through the conduit 42 to the waste tank or reservoir 26.

Reaction flow system 14 is provided with a sample solvent reservoir 32 and one or more reagent reservoirs 34. Solvent from the reservoir 32 is pumped by liquid pump 36 through fluid conduit 38, through the pump 36 and through the fluid conduit 39 to stream sampling valve 16 where a relatively pulse free flow is maintained. Conduit 38 may contain a bubble trap (not shown) between reservoir 32 and pump 36. Conduit 39 can be provided with a flow meter (not shown), and pressure gauge (not shown) and filter (not shown) between pump 36 and stream sampling valve 16 if desired. Reagent is pumped from the reservoir 34 by liquid pump 48 through fluid conduit 50, through the pump 48 and through the fluid conduit 51 to the mixer 52. Conduit 50 can be provided with a bubble trap (not shown) between reservoir 34 and pump 48. Conduit 51 can be provided with a flow meter (not shown) and filter and pressure gauge (not shown) between the pump 48 and the mixer 52 if deemed desirable. Samples cut out of conduit or probe 20 and placed into the sample solvent stream by valve 16 are conducted without air bubbles where only a liquid-liquid interface exists through the fluid conduit 62, a stirred dilution chamber 78 and a fluid conduit 44 to the mixer 52. The mixed liquids then flow through fluid conduit 64 to reaction or heating coil 66 through fluid conduit 46, to the cooling coil 68, through the fluid conduit 58 to a detector 70 that can be a colorimeter or other type of instrument for analytical measurement purposes and then through the fluid conduit 60 to the waste tank 74. As the stream of liquid flows through the detector 70, the detector's output which represents the presence or absence of color, fluorescene or other property of the fluid stream that is being measured is sent via the electrical conductor 90 to the computer 82.

Since the sample flow system 12 and reaction flow system 14 are separate entities, air or gas segmentation is eliminated in the reaction system. The common element of the two systems is stream sampling valve 16 which automatically transfers a predetermined amount of sample from sample flow system 12, or, more precisely, from fluid conduit or probe 20, to fluid conduit 62 in the reaction flow system 14.

Stream sampling valve 16 functions to slice out a measured volume of the sample from fluid conduit or probe 20 of the sample flow system 12 and inject this sample into the reaction flow system 14. It is important that only the sample and neither the air nor the wash solution be injected into reaction system 14. Many portions of the apparatus for the determination of concentrations 10 thus far described except for the stirred dilution chamber 78 and the computer 82 are conventional and are described in U. S. Pat. No. 4,013,413 that, as previously indicated, is incorporated herein by reference.

As illustrated in FIG. 3, the apparatus for the determination of concentrations includes a stirred dilution chamber 78 that is connected to the sampling valve 16 and the mixer 52 by the respective fluid conduits 62 and 44. This stirred dilution chamber 78 is extremely important to the proper functioning of the apparatus for the determination of concentrations 10 since it allows, the detector 70 to view a concentration versus time relationship such as that illustrated in FIG. 2. The construction of the stirred dilution chamber 78 will be hereinafter described in considerable detail. The apparatus for the determination of concentrations 10 also includes a computer 82 with its data display 84 and this computer 82 is electrically connected to the sampling valve 16, sample withdrawal pump 24 and the detector 70 via the respective electrical conductors 86, 88, and 90 for the electrical transmission of information to and from the computer 82 for the purpose of controlling the various system components and calculation of concentrations through analysis of standards and associated standard curves.

Figure 4:
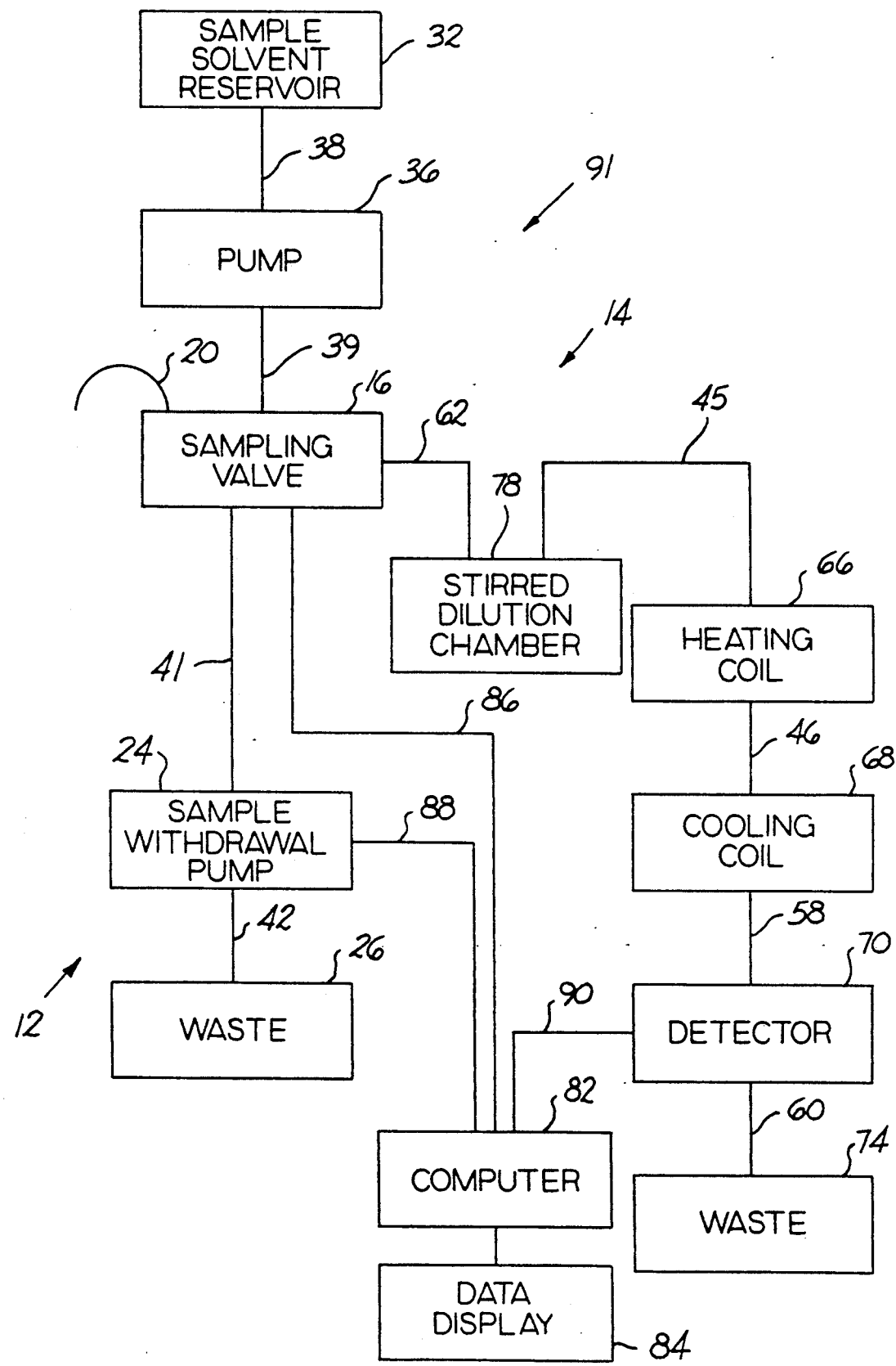
FIG. 4 is a block diagram of a second embodiment of the apparatus for determination of concentration.

FIG. 4 illustrates a modification of the apparatus for determination of analyte concentrations that is designated generally by the number 91. The apparatus for determination of analyte concentrations 91 is a simplification of the equipment set forth and described in FIG. 3. Specifically, reagent reservoir 34, conduit 50, pump 48, conduit 51 and mixer 52 have been removed. Stirred dilution chamber 78 is connected directly to heating coil 66 via conduit 45. The addition of the stirred dilution chamber to a conventional FIA system permits the mixing and interaction of desired chemicals added to the sample solvent with analytes of interest in the sample. For determination of analyte concentrations requiring the addition of chemicals in onestep, this modification obviates the need for addition of a separate reagent an example of such a determination is pH in samples. As indicated in FIG. 4, both the heating coil 66 and the cooling coil 68 are optional.

Figure 5:
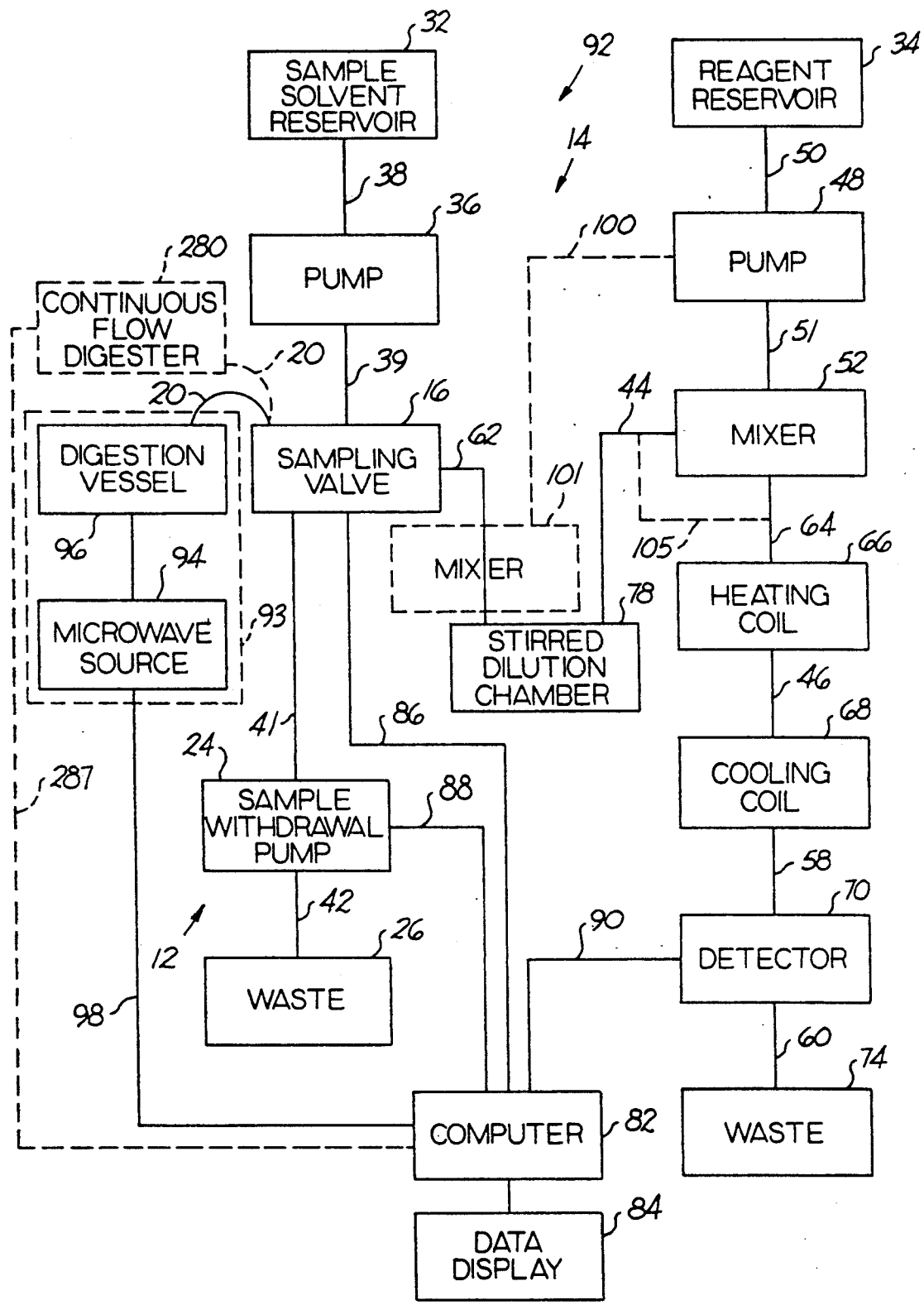
FIG. 5 is a block diagram of a third embodiment of the apparatus for determination of concentration.

FIG. 5 illustrates schematically a modification of the apparatus for determination of concentrations that is represented generally by the number 92. The apparatus for determination of concentrations 92 illustrated in FIG. 5 comprises all of the structure of the previously described apparatus for determination of concentrations 10 set forth in FIG. 3. However, in addition, the apparatus for determination of concentrations 92 also comprises means for digestion of the sample 93 that includes an energy source which in the preferred embodiment is a microwave energy source 94 that is operatively connected to and provides energy to a digestion vessel 96 that forms part of the digestion means 93. The digestion vessel 96 is in turn operatively connected to the sample probe 20 that is connected to the sampling valve 16. The microwave energy source 94 is connected to and controlled by the computer 82 via the electrical conductor 98. As illustrated in FIG. 5, an optional conduit represented by the dashed line 100 is provided that connects the conduit 62 to the pump 48 via mixer 101 that is inserted into the conduit 62 which also connects the mixer 101 to stirred dilution chamber 78. When this option is used, the fluid conduit 51 and the mixer 52 are removed from the system and the optional fluid conduit 105 indicated by the dashed line connects the fluid conduit 44 to the fluid conduit 64.

Figure 6:
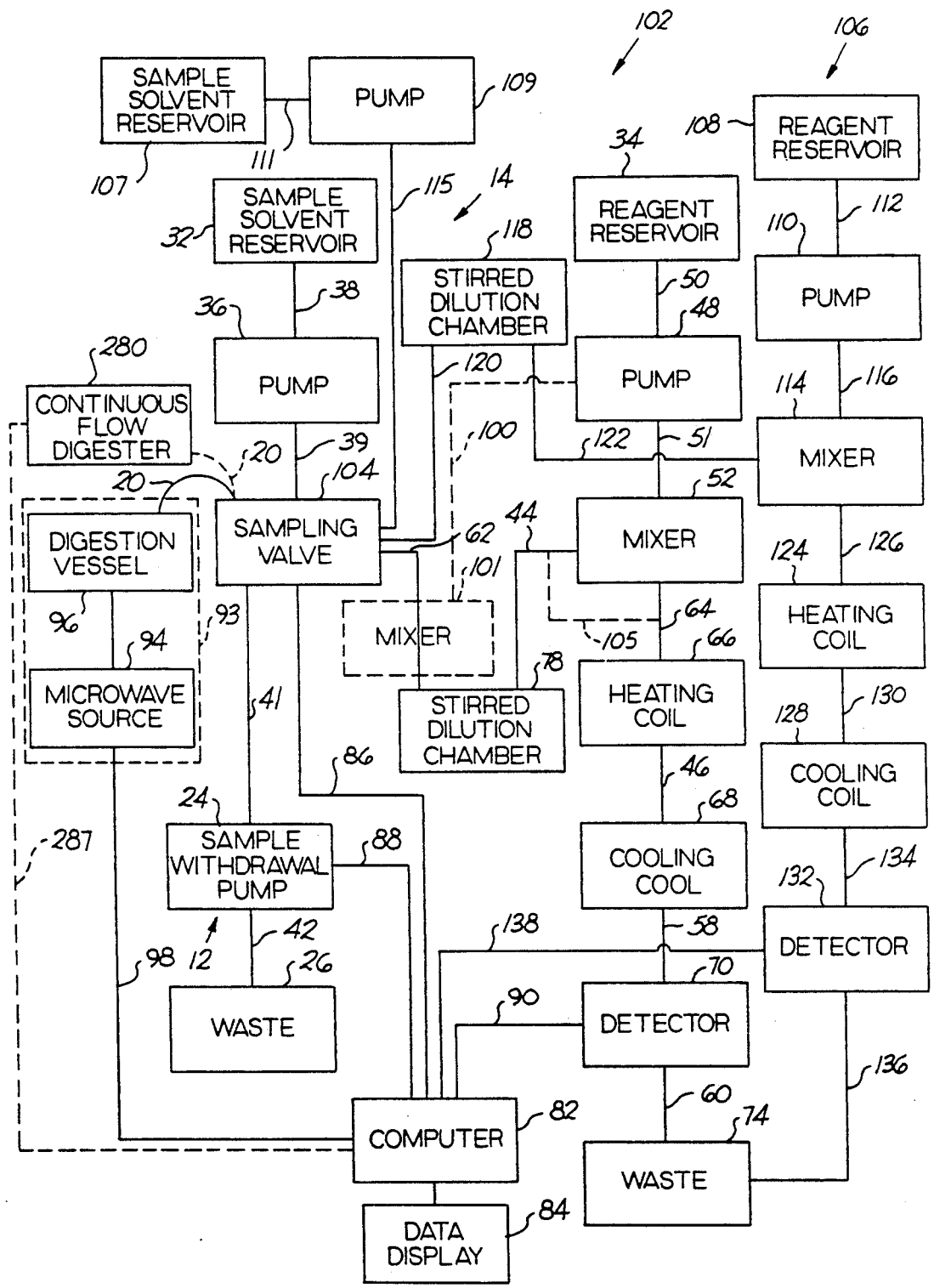
FIG. 6 is a block diagram of a fourth embodiment of the apparatus for determination of concentration.

FIG. 6 illustrates an additional embodiment of the apparatus for the determination of concentrations that is designated generally by the number 102. The apparatus for the determination of concentrations 102 comprises all of the equipment set forth and described with respect to FIG. 5 except that a ten port sampling valve 104 is substituted for the previous six port sampling valve 16. The apparatus for the determination of concentrations 102 includes an additional reaction flow system designated generally by the number 106 that enables the apparatus for the determination of concentrations to perform two analyses on the same sample that would be desirable when two analytes are to be separately measured. The additional reaction flow system 106 includes a sample solvent reservoir 107 connected to a pump 109 by the fluid conduit 111 that is in turn connected to the sampling valve 104 by the fluid conduit 115. In addition, this additional reaction flow system includes a reagent reservoir 108 connected to a pump 110 by a fluid conduit 112 that is in turn connected to a mixer 114 by a fluid conduit 116. The additional reaction flow system 106 also includes a second stirred dilution chamber 118 that is connected to the sampling valve 104 by the fluid conduit 120 and to the mixer 114 by the fluid conduit 122.

As illustrated in FIG. 6, the additional reaction flow system 106 also includes an optional heating coil 124 connected to the mixer 114 by the fluid conduit 126 and an optional cooling coil 128 connected to the heating coil 124 by the conduit 130. The optional cooling coil 128 is connected to a detector 132 by the fluid conduit 134 and the detector 132 is connected to the waste reservoir 74 by the fluid conduit 136. The detector 132 is also electrically connected to the computer 82 by the electrical conductor 138.

Figure 7:
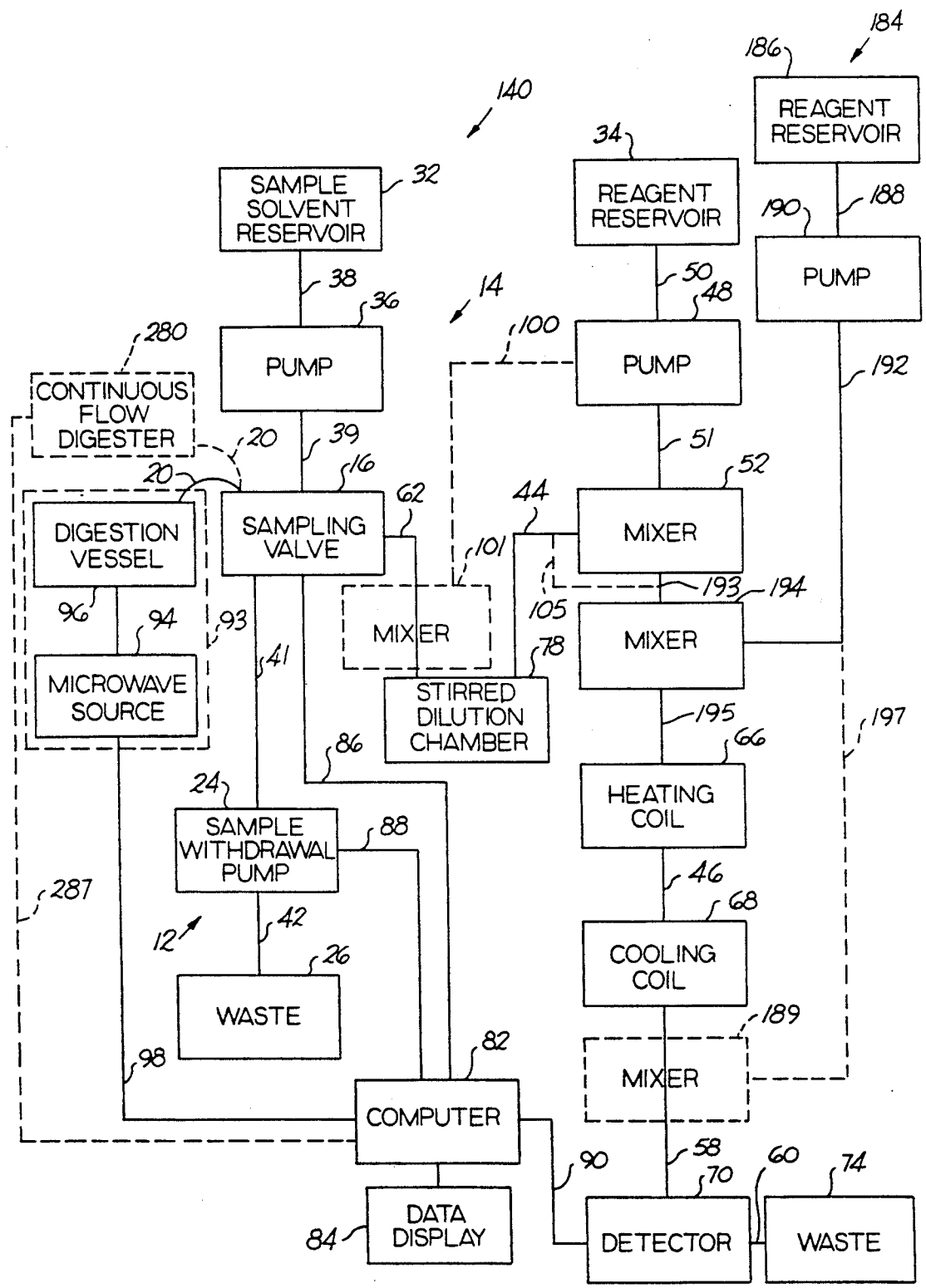
FIG. 7 is a block diagram of a fifth embodiment of the apparatus for determination of concentration.

FIG. 7 illustrates an additional embodiment of the apparatus for determination of concentration designated generally by the number 140. The apparatus for determination of concentration 140 comprises the same apparatus previously described with respect to and set forth in FIG. 5. However, this embodiment of the apparatus for determination of analyte concentration 140 is designed to add an additional reagent to accomplish the determination. An example of this would be the measurement of phosphorus. This embodiment of the apparatus for determination of analyte concentration 140 includes an additional reagent stream designated generally by the number 184. The additional reagent stream 184 includes a reagent reservoir 186 that is connected by a fluid conduit 188 to a pump 190 that is in turn connected to a mixer 194 by a fluid conduit 192. The mixer 52 is connected to mixer 194 by a fluid conduit 193 and the mixer 194 is connected to the optional heating coil by a fluid conduit 195. Also, as illustrated in FIG. 7, by the dashed line 197 and dashed block 189, the mixer 189 may alternatively be located between the optional cooling coil 68 and the detector 70.

Figure 8:
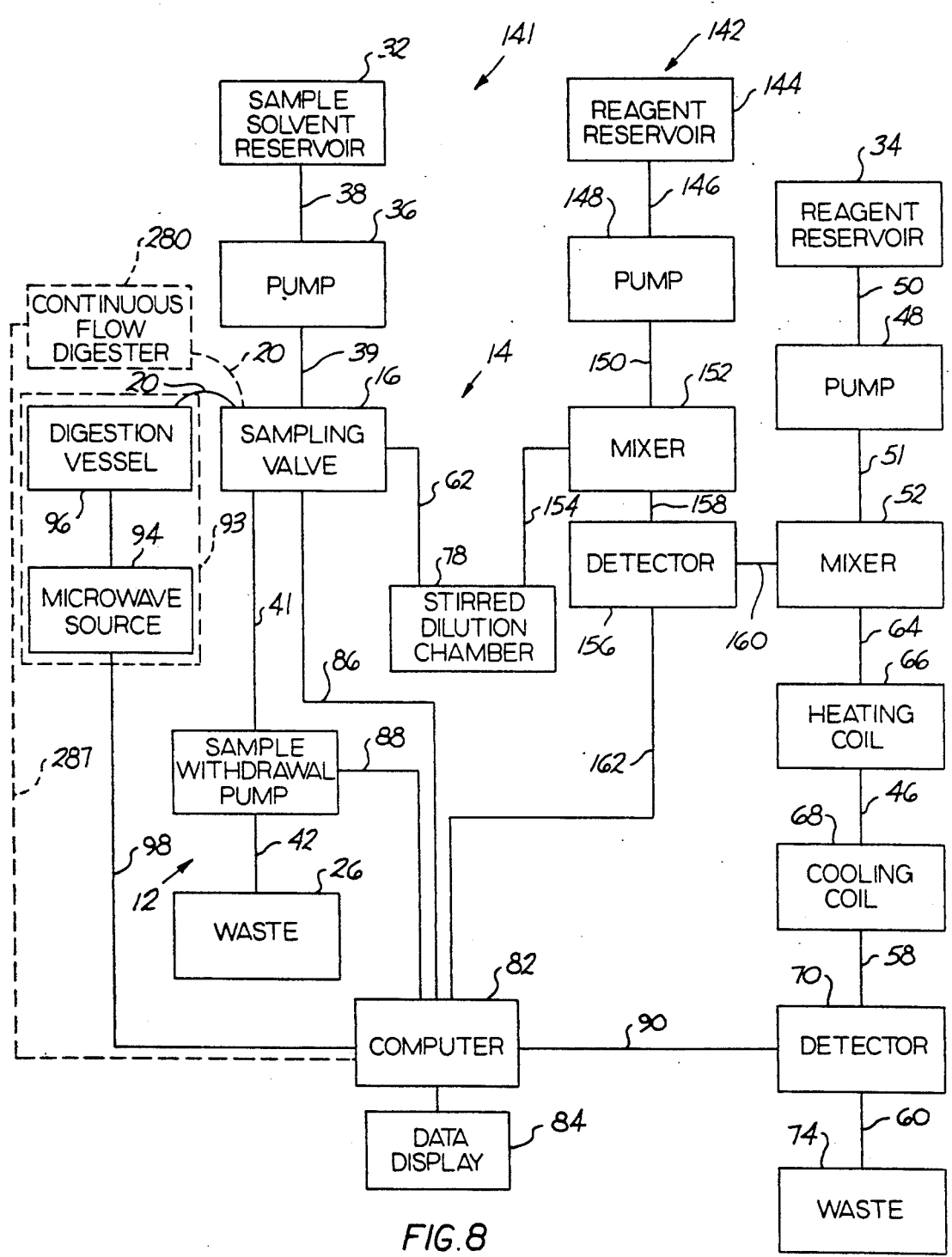
FIG. 8 is a block diagram of a sixth embodiment of the apparatus for determination of concentration.

FIG. 8 illustrates an additional embodiment of the apparatus for determination of analyte concentrations designated generally by the number 141. The apparatus for determination of analyte concentration 141 comprises the same apparatus previously described with respect to and set forth in FIG. 5. However, this embodiment of the apparatus for determination of concentration 141 is also designed to carry out an additional analysis of a sample that does not require heating and cooling and in which the reaction time is minimal. An example of this would be the measurement of pH. This embodiment of the apparatus for determination of concentration 141 includes an additional optional detection channel designated generally by the number 142. The optional detection channel 142 includes a reagent reservoir 144 that is connected by a fluid conduit 146 to a pump 148 that is in turn connected to a mixer 152 by the fluid conduit 150. The mixer 152 is connected to the stirred dilution chamber by the fluid conduit 154 and the mixer 152 is also connected to a second detector 156 by the fluid conduit 158. The second detector 156 is in turn connected to the mixer 52 by a fluid conduit 160. The second detector 156 is electrically connected to the computer 82 by an electrical conduit 162.

FIGS. 9 and 10 illustrate a top and a sectional view of the stirred dilution chamber 78 that is an important part of all of the embodiments of the invention set forth in FIGS. 3 through 8. As illustrated, the stirred dilution chamber 78 comprises a generally cylindrical shaped hollow container 164. The hollow container 164 must be made from a magnetically permeable material and in the preferred embodiment the material is a glass container known as a Microflex Vial that is available from Kontes Corporation of Vineland, N.J. or may be constructed of Teflon or similar material with similar dimensions.

As illustrated, the interior of the cylindrical shaped hollow container 164 has a funnel shaped inward sloping bottom surface 166 and a dome shaped or partial spherical shaped upper surface 168. A hole 170 extends into the upper portion of the container 164 and through the dome shaped surface 168 and an inlet tube 172 extends through this hole 170 and into the interior of the hollow container 164. The inlet tube 172 terminates with its outlet end 174 located substantially in the center of the interior of the hollow container 164 and just above and adjacent to the stirrer magnet 180. Another hole 176 is located in the top of the hollow container 164 and this hole 176 extends through the uppermost portion of the spherical surface 168. This hole 176 receives an outlet tube 178 which does not enter the container 164 but whose edges are flush with the inner top surface 168.

As illustrated in FIG. 10, the stirrer magnet 180 that is located within the hollow container 164 adjacent the outlet end 174 of the inlet tube 172 is loose and is coated with a plastic 182. An electromagnet 184 is located outside of the hollow container 164 adjacent the loose stirrer magnet 180 in position to cause the loose stirrer magnet 180 to rotate as the magnetic field in the electromagnet is alternated due to the action of the electromagnet activating circuit that is designated generally by the number 186.

Figures 11, 13:
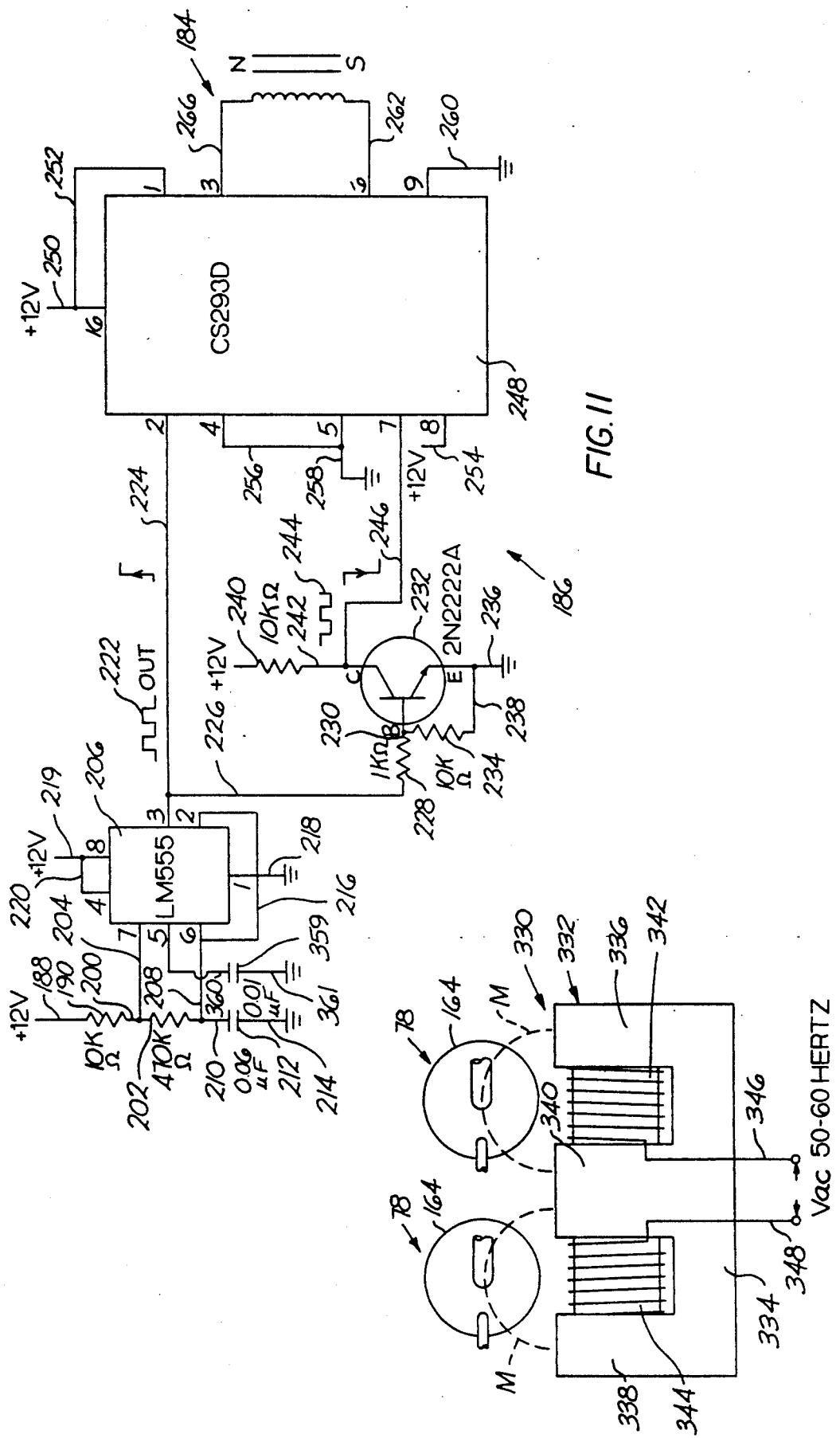
FIG. 11 is a circuit diagram of the electromagnet activating circuit and the electromagnet illustrated in FIG. 10.
FIG. 13 is a top view of an alternative embodiment for driving the magnet located in the dillution chamber illustrated in FIGS. 9 and 10.

The electromagnet activating circuit 186 is set forth in the circuit diagram in FIG. 11. As illustrated, the activating circuit 186 has a lead 188 that is connected to a source of a +12 volts d.c. that can be a suitable battery or the like (not shown) and to a 10K resistor 190. The resistor 190 is in turn connected by the lead 200 to a 470K resistor 202 and a lead 204 that is connected to pin 7 of a LM555 that is a pulse generator 206. The other side of the resistor 202 is connected via the lead 208 to pin 6 of the pulse generator 206, and a lead 210 is also connected to this end of the resistor 202 and a 0.06 $\mu f$ farad capacitor 212 that is in turn connected to ground by lead 214. Pins 2 and 6 of the LM555 are connected together by the lead 216 and pin 1 is connected to ground by the lead 218. Pins 4 and 8 of the pulse generator 206 are connected via leads 219 and 220 to the source of positive 12 volts d.c. The 0.01 $\mu f$ capacitor is connected to pin 5 of the LM555 via lead 360 and to ground via lead 361. This arrangement results in a square wave output designated 222 from pin 3 on lead 224.

The pulsed voltage wave form 222 on lead 224 is also fed via electrical lead 226 to a 1K resistor 228 and then via lead 230 to the base B of a 2N2222A NPN transistor 232. Lead 230 is also connected to 10K resistor 234 and both the emitter E of the transistor 232 and the resistor 234 are connected to ground via the leads 236 and 238. The collector C of the transistor 232 is connected to a 10K resistor 240 via lead 242 which is in turn connected to the source of +12 volts d.c. This results in a pulsed output 244 on lead 246 that is the inverse of the wave form 222 on lead 224.

The pulsed output 222 on lead 224 and the inverted pulses 244 on lead 246 are fed to the respective pins 2 and 7 of a CS293D switch 248 that contains four transistors and functions as an H switch that requires both the signal 222 and its inverse 244 for switching purposes. It will be noted that pins 1 and 16 and 8 of the switch 248 are connected via leads 250, 252, and 254 to the source of +12 volts d.c. and that pins 4, 5, and 9 are connected to ground by the leads 256, 258, and 260. The resulting output from the switch 248 is from pins 3 and 6 on leads 262 and 266 that are connected to the electromagnet 184. The polarity of the output on leads 262 and 266 is rapidly reversed to reverse the magnetic poles N and S of the electromagnet 184 at a frequency of substantially fifty to seventy Hertz in the preferred embodiment.

FIG. 12 is a sectional view of the stirred dilution chamber 78 illustrated in FIGS. 9 and 10, but showing an alternative embodiment for driving the stirrer magnet 180. As illustrated in this embodiment the stirrer magnet 180 is are driven by the magnetic force from an elongated permanent magnet 264 that rotates outside of the cylindrical shaped hollow container 164 of the stirred dilution chamber 78. As indicated, the ends of the permanent magnet have either a north N or a south S pole that will cause either an attraction or a repulsive force with the adjacently located north N or south S pole of the stirrer magnet 180 located within the hollow container 164. This will result in the rotation of the stirrer magnet 180 which in turn will cause rapid mixing of any fluids within the hollow container 164. The permanent magnet 264 has its center portion rigidly secured to the end of a rotatable motor shaft 266 that extends from a conventional small size a.c. or d.c. motor 268 that is connected to an a.c. source (not shown) or a battery 270 by the electrical conductors 272, 274, 276, and the manually operated switch 278. Magnets 184 and 264 may alternatively be placed below the container 164 to drive the magnet 180 inside the container 164. This alternative positioning of the magnets 184 and 264 is not the preferred location if maximum speed of movement of the magnet 180 is to be realized.

FIG. 13 illustrates a top view of an alternative means for driving the magnet 180 located within the container 164 of the stirred dilution chamber 78 that is designated generally by the number 330. The magnet driving means 330 comprises an iron laminated E-shaped core 332 with a base portion 334, two outer projections 336 and 338 and a center projection 340. A wire bobbin or wound wire coil 342 is located between the outer projection 336 and the inner projection 340 and a similar wire bobbin or wound wire coil 344 is located between the respective outer and inner projections 338 and 340. The wound wire coils 342 and 344 have the respective leads 346 and 348 extending from them and as indicated a voltage Vac obtained from an alternating current source having a frequency of between approximately 50 and approximately 60 Hertz is applied to the leads 346 and 348. In the preferred embodiment Vac should be substantially 8 volts. This 8 volts may be obtained from a conventional source of alternating current by means known in the art.

The variable voltage Vac applied to the coils 342 and 344 via the respective leads 346 and 348 causes the variable alternating magnetic flux designated by the latter M in FIG. 13 that causes the rotation of the magnet 180 located in each of the two stirred dilution chambers 78 resulting in the stirring of any liquid within the hollow chambers 164. Of course, if desired, only one stirred dilution chamber 78 need be present, but the magnet driving means 330 offers the flexibility of adding an additional stirred dilution chamber 78.

Figure 14:
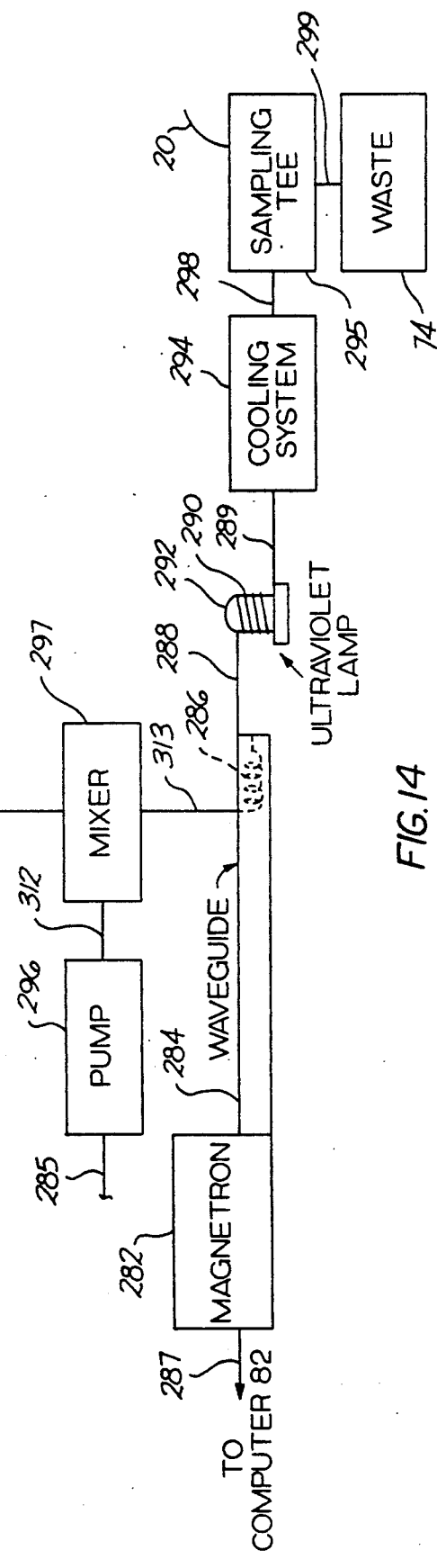
FIG. 14 is a side elevational view of a continuous flow digester that can form part of the present invention.

FIG. 14 illustrates a continuous flow digester designated generally by the number 280 that can be used in place of the previously described digestion means 93 comprising the microwave energy source 94 and the digestion vessel 96 set forth in FIGS. 5, 6, 7 and 8. The continuous flow digester 280 comprises a magnetron 282 with a substantially straight waveguide 284 extending from it and a coil of microwave permeable tubing 286 coiled inside the outer end portion of the waveguide 284. A length of tubing 288 extends from the coiled tubing 286 to a portion of tubing 290 that is coiled around an ultraviolet lamp 292 and from there a connected tubing 289 goes through a cooling system 294. A section of tubing 298 is connected to the tubing 289 at the cooling system 294 and extends to a tee fitting 295 that is in turn connected to the sample probe 20. The tee 295 is also connected to a fluid conduit 299 that is connected to a waste receptacle such as the receptacle 74. It should be noted that the ultraviolet lamp 292 and its associated coiled tubing 290 are optional and may not be needed for some purposes.

As illustrated in FIG. 14, the continuous flow digester 280 includes an oxidant/catalyst reservoir 281 and a pump 291 that is connected to the reservoir 281 by the fluid conduit 283. The pump 291 is in turn connected to a mixer 297 by the fluid conduit 293 and the mixer 297 is in turn connected to the digester coil 286 by the fluid conduit 313. The continuous flow digester 280 also includes a pump 296 that is connected to a sample solution inlet tubing or conduit 285 and the pump 296 is in turn connected to the mixer 297 by a fluid conduit 312. The continuous flow digester 280 also includes an optional oxidant/catalyst pumping system 301 illustrated in dashed lines. This system 301 includes an oxidant/catalyst reservoir 302 that is connected to a pump 304 by a fluid conduit 306. The pump 304 is connected to a mixer 310 by a fluid conduit 308. The mixer 310 is connected to the pump 291 and to the mixer 297 by the fluid conduit 293.

Figure 15:
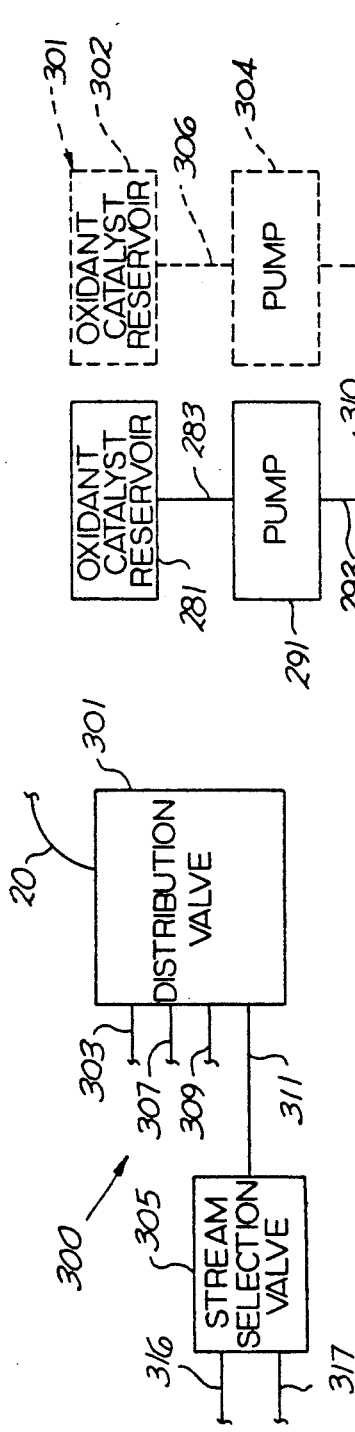
FIG. 15 is a block diagram of a distribution valve that can form part of the present invention.

FIG. 15 illustrates a block diagram of a distribution valve system designated generally by the number 300 that may be utilized at the entrance to the sample side of the sampling valve 16 or 104 set forth in the previously described FIGS. 3 through 8. As illustrated, the distribution valve system 300 includes a distribution valve 301 with a plurality of sample stream input conduits designated by the numbers 303, 307, 309, and 311. As illustrated, the distribution valve system 300 also includes a stream selection valve 305 that is connected to the fluid conduit 311. As illustrated, the stream selection valve 305 is connected to an online input fluid conduit 316 and a manual input fluid conduit 317 which permits the connection of the manual fluid conduit 317 with the fluid conduit 311 by the appropriate operation or switching of the stream selection valve 305. Normally, the stream selection valve 305 would be set so that the online fluid conduit 316 is connected to the fluid conduit 311.

The apparatus for determination of concentrations 10, 91, 92, 102, 140 and 141 of the respective FIGS. 3, 4, 5, 6, 7 and 8 are made in the following manner. All of the basic structure of the apparatus for the determination of concentrations 10 illustrated in FIG. 3 including the reservoirs 32 and 34, pumps 36 and 48, sampling valve 16, sample withdrawal pump 24, waste receptacles 26 and 74, heating coil 66, cooling coil 68, mixer 52, and the detector 70 are in themselves known in the art. The same is true of the microwave energy source 94 and digestion vessel 96 of FIG. 5 and the items that make up the additional detection channel 106 in FIG. 6 and the items that make up the additional reagent stream or channel 184 in FIG. 7 and the optional detection channel 142 of FIG. 8. The computer 82 is a microprocessor that is assembled using conventional techniques known in the art and all of the electrical conductors associated with the computer 82 are standard and well known in the art.

The stirred dilution chamber 78 in FIGS. 9, 10, 12, and 13 is a non-conventional item and its proper construction is necessary for the proper operation of the invention. The hollow cylindrical container 164 is made from glass, Teflon or similar material using conventional plastic molding techniques. It is important that the outlet end portion 174 of the inlet tube 172 be located close to the location of the coated stirrer magnet 180. It is also very important that the top surface of the interior of the container 164 have the dome or rounded shaped surface 168 and the hole 176 for the outlet tube 178 must be located at the highest point on this surface 168 to ensure only fully mixed sample and carrier are carried to the detector 70 and to assist in cleaning any air bubbles accidentally introduced into the system from the system. It is also important that the interior volume of the container 164 be much greater than the volume of the sample. Assuming that the sample volume is some 20 microliters then the interior volume of the container 164 should be substantially some 300 microliters with a minimum of substantially 200 microliters. In the preferred embodiment the minimum interior volume of the container 164 should be a minimum of substantially ten times the sample volume. The ratio of the volume of the chamber to the volume of the sample must be no less than 2:1 and is preferably 10:1 or greater. The ratio may be changed within these preferred ratios, to increase or decrease the minimum level of detection. The maximum will, of course, depend upon the expected concentrations of the substance to be measured in the sample.

The shape of the interior chamber of the container 164 is not critical provided good mixing occurs as close to instantly upon sample entering the chamber as possible and no dead flow areas exist so that continuous mixing occurs between the carrier stream and sample. It is important that sufficient turbulence be found in the chamber to effect the mixing.

The electromagnet activating circuit 186 set forth in FIG. 11 is constructed using techniques known in the art from the various indicated components. It will, of course, be appreciated that equivalent components known in the art can be substituted for the specific designated components. The magnet driving means 330 circuit including the laminated core 332 illustrated in FIG. 13 is made up from simple transformer parts that are readily available in a manner well known to those skilled in the art.

With the previously indicated additions, the construction of the apparatus for determination of concentrations 10, 91, 92, 102, 140 and 141 of the respective FIGS. 3, 4, 5, 6, 7 and 8 is similar to that of the apparatus set forth in U.S. Pat. No. 4,013,413. However, for best results the tubing through which the sample flows to and from the stream sampling valve and which is used in the reaction flow system must have a small bore and be made of material inert to the fluids flowing through it. Tubing having an internal diameter of from about 0.028 to about 0.009 inches, that is, 22 to 32 American Wire Gauge (AWG), are suitable. Tubing having an internal diameter of about 0.018 inches (26 AWG) is preferred. Inert materials suitable for use in constructing the stream sampling valve and the tubing are stainless steel, polytetrafluoroethylene (Teflon) and polychlorotrifluorethylene (Kel F) or other such inert materials.

The stream sampling valve 16 and 104 must be designed, constructed, and timed to transfer a known, predetermined volume of sample only from the sample flow system to the reaction flow system. The mixing volumes in the stream sampling valve must be very small. In the preferred embodiment of the invention no mixing or an extremely inconsequential amount of mixing takes place in the stream sampling valve. A standard High Performance Liquid Chromatography sampling valve, available from Valco or Rheodyne of respectively Houston, Tex. and Cotati, Calif. is suitable for this purpose. The valve may be either 6 port or 10 port construction. A port being an entrance on a stator which connects to a groove on the rotor to connect one port to another port internally such that when the rotor is rotated, different ports may be connected. Two of the ports have a fixed loop between them, which is known as the sample loop. In the load position, the sample inlet is connected to the sample loop, which is further connected to an outlet port which is connected to the sample withdrawal pump which is connected to waste. At the same time, the carrier stream is internally connected to the port leading to the analytical portion of the system. When the valve is cycled, the carrier stream is connected to the sample loop and the output of the sample loop is connected to the analytical portion of the system. The sample inlet is now connected to a port leading to waste. This permits the interspersing of a sample between two segments of the carrier stream. In the case of a ten port valve, two sample loops are connected to a single sample source and two carrier streams are independently connected to two different analytical portions of the system.

The preferred time required for the valve to make a change of port connections is the smallest fraction of a second approaching zero which is possible. In addition, the actuating means must be connected to a timing device so that the valve is rotated at a proper time to transfer sample solution only and not carrier solution or wash solution when attached to an autosampler. The stream sampling valve must also be constructed and properly connected so that the sample solution will continue to flow to waste while the sample in the sample loop is being injected into the reaction flow system. Concurrently, the carrier solution must always flow to the reaction flow system either through the sample loop or through the bypasses.

The previously discussed narrow bore tubing is conducive to the desired high flow rate through the reaction flow system. Although the preferred flow rate presently ranges from 1 to 8 ml per minute, flow rates covering a range from 0.1 to 25 ml per minute are attainable with the apparatus of this invention. However, even with the narrow bore tubing, it would not be possible to attain high flow rates and precision if the connecting fittings were such that they allowed mixing of fluids. Consequently all connecting fittings in the invention must be minimum dead volume fittings, that is, ones that will maintain sample integrity by providing no extra volume and minimal turbulence, in which the flowing liquids can mix.

The previously described distribution valve 300 of FIG. 4 may be employed at the entrance to the sample side of the sampling valve 16 or 104. In this way, a multiplicity of sample streams 303, 307, 309 or 311 may be selected, one or more of which can be other sample streams or standards to confirm the analytical and quantitative nature of the device. This sampling valve may be actuated electromechanically, pneumatically or manually in a manner known to those skilled in the art. A stream selection valve 305 may be used to feed the distribution valve 300 through the conduit 311. The valve 305 is shown as a 3 port valve, but may be much larger allowing a multiplicity of sample links to be sampled. In this way a single sample may be manually and easily introduced into an online instrument by simply opening the conduit 317 which becomes a manual sample port.

The pumps that deliver sample solvent and reagents into the system should be positive displacement pumps capable of delivering liquid at 0.1 to 25 ml per minute at up to 200 psi, with a delivery precision of +/−1.0% of delivered volume. When a peristaltic pump is used, the pulsation may be limited by decreasing the size of the orifice on the outlet side. Care must be taken to maintain the tubing used in a peristaltic system to insure consistent flow rates. All pump delivery at the point of delivery into the system should be relatively pulse free which may be accomplished by a number of devices known in the art.

The mixer, such as the mixer 52, where the sample solvent stream joins the reagent stream, must provide good mixing of the two streams and yet maintain sample integrity. This has been attained by using T-type minimum dead volume mixers known as Tee, available from Alltech Corporation of State College, Pa. Other minimum dead volume mixers known in the art may also be used. The only requirements are that they provide good mixing and maintain sample integrity.

Since the reaction product being measured, whether it be by color or some other measurable quality, is developed in the reaction coil, such as the coil 66, which may or may not be heated, the coil must be long enough for the reaction to take place. The apparatus of this invention has been successfully used with coils from about 1 to 100 feet long. However, the invention is not limited to that range of lengths. The only requirement is that it be long enough for the sample and reagent to react. The internal diameter of the reaction coil should be the same as that of the tubing to which it is connected in the reaction flow system in order to maintain sample integrity.

A cooling coil, such as the coil 68, may be used to cool the flowing liquid from the reaction coil 66 to the temperature of the colorimeter or other analytical instrument if necessary to minimize schlerin effects of heat during optical measurement. The internal diameter of the cooling coil 68 should be the same as that of the reaction coil 66.

In order to maintain the sample integrity until the desired analytical results are obtained and recorded, the colorimeter, fluorimeter, or other analytical instrument that comprises the detector 70 must be equipped with a low volume cell with a fairly long optical path length. Flow cells having optical path lengths of from 0.1 to 20 millimeters and cell volumes of from less than 1 microliter to 20 microliters have been successfully used in the apparatus of this invention. However, the apparatus is not limited to volumes and path lengths of these capacities and dimensions.

Flow meters (not shown) and pressure gauges (not shown) that are known in the art can be used and are suggested in the reaction flow system to measure flow rates and pressures. In-line filters (not shown) that are also known in the art can be used to remove dust and particles and bubble traps (not shown) known in the art can be provided to remove air bubbles. The only requirements for these parts of the apparatus are that they perform their intended functions and hence their use need not be described since their use is obvious to one skilled in the art.

The apparatus of this invention is useful for the analysis of up to 100 samples per hour with high precision. In fact, with respect to precision at high rates of analysis, the average coefficient of variation was found to be about 1.0%.

In the case of a colorimetric detection system, the system components are: an energy source; a fixed path flow cell; a detector for light energy; and an amplification circuit. A stable light source which consists of a light emitting diode which is not sensitive to temperature and is powered by a stable d.c. voltage source that is known in the art is suitable for the apparatus of the invention. The monochromicity of light is controlled either through the color of the diode and/or by an optical filter. A light sensitive diode may be used for the detectors 70, 132 and 156 since the detection does not require the linearity of response of a more sophisticated detector. Since it is necessary to only detect the presence or absence of the property measured, the band pass of the monochromatic light can be quite large provided no other constituent of the sample has an overlapping absorbance. In the preferred embodiment the detector or detector system is manufactured from standard electronic components known in the art. Other detectors or systems can be used for ultraviolet, luminescent, fluorescent or infrared systems. The accuracy of the path length of the flow cell is not critical since Beer's Law will not used for calculations, but it should be sufficiently small to prevent uncontrolled dilution of the analyte.

The minimum electronics circuitry for the detector 70 is a preamplifier and an amplifier with a gain control from the preamplifier. In normal operation the detector 70 is set in the middle of the amplifier range so that we can monitor reactions in which the peak is due to either an increase or decrease of color.

A trigger level is used to start a timer in order to measure the width of the peak. The establishment of a trigger level, which is a preset voltage difference from the baseline, may be accomplished in several ways. One way is to use an analog comparator circuit and another is to use a digital circuit. It has been discovered that a far superior method is to use the microprocessor of the computer 82 to compensate for changes in the baseline and permit a constant relationship between the baseline and the trigger level which is the level at which the clock is turned on or off to measure the peak width. In this way, the baseline may drift and not affect the true differential between the baseline and the trigger level which is essential for accurate calculations. In this manner different kinds of reagents having similar wavelength requirements may be used without resetting the baseline and/or comparator values.

The detector 70 generates an analog signal which is transmitted to the standard digital microprocessor system of the computer 82. The signal is converted from analog to digital through a standard analog to digital converter that is part of the computer 82. This computer 82 has several jobs to perform in the system that are:

1. calculation of the analytical results based on data received from the detectors 70, 132 and/or 156;
2. control of the system pertaining to timing and selection of sampling stream, standards, and their proper introduction into the system; and
3. acting as a user interface allowing the operator to manipulate the system in a manual, semiautomatic mode.

However, these need not be discussed in detail since they are well known to those skilled in the art.

The continuous flow digester 280 illustrated in FIG. 13 uses a magnetron 282 that is commercially available from any household microwave oven such as those manufactured by Samsung Corporation, Seoul, Korea and the connected waveguide 284 is a standard microwave waveguide available from Phelps Dodge. The optional ultraviolet lamp 292 is a mercury ultraviolet source available from PBL ElectroOptics, Inc. of West Newbury, Mass. and the cooling system 294 comprises a coil of Teflon tubing (some are 20 feet long) placed in a liquid cooling bath such as Model D8G, available from Haake, Inc. of Valencia, Calif. Or the coil of tubing can be placed in close association with solid state cooling devices known to persons skilled in the art. The tubing 286 should be made from Teflon or other similar tubing that is permeable to microwaves and in the preferred embodiment it should nominally have a 0.5 to 2.0 millimeter inside diameter. The length of the tubing will be dependent on the digestion time and the flow rate of the solution and can be determined by those skilled in the art once these are known. In use, the digester 280 is substituted for the microwave energy source 94 and the digestion vessel 96 illustrated in FIGS. 5 through 8 and is connected as illustrated in these figures to the sample probe 20.

The apparatus for determination of concentrations 10, 91, 92, 102, 140 and 141 of the respective FIGS. 3, 4, 5, 6, 7, and 8 are used and the method of the invention is carried out in the following manner. First, considering the apparatus for the determination of concentrations 10 illustrated in FIG. 3, the reservoirs 32 and 34 are filled with suitable solvent and reagent, respectively. The pumps 36 and 48 are started resulting in the pumping of sample solvent from the reservoir 32 through the conduit 38, through the pump 36 and through the conduit 39 to the sampling valve 16 and the pumping of reagent from the reservoir 34 through the conduit 50, through the pump 48 and through the conduit 51 to the mixer 52. The withdrawal pump 24 is also turned on and the sampling valve 16 through the sample probe 20 picks up a sample that is then transported into the sample solvent stream by the sampling valve 16. The control of the sampling valve 16 and the sample withdrawal pump 24 is under the direction of the computer 82 through the respective electrical conductors 86 and 88. Waste from the sample withdrawal pump 24 passes through the conduit 42 to the waste reservoir 26. The sampling valve 16 functions in the previously indicated manner.

From the sampling valve 16, the sample travels through the conduit 62 to the stirred dilution chamber 78 where the sample is diluted rapidly in the previously indicated manner. This diluted sample then is transferred through the conduit 44 to the mixer 52. From the mixer 52 the diluted sample and reagent mixture flows through the conduit 64 to the heating coil 66 where a chemical reaction can take place and from the heating coil 66 the fluid then passes to a cooling coil 68 through the conduit 46. From the cooling coil 68, the mixed and diluted sample goes through the conduit 58 to the detector 70 that detects the presence and then the absence of the sample under analysis. The computer 82 obtains this information via the electrical conductor 90 and uses it to determine the concentration of the sample being analyzed in the previously indicated manner. Fluid from the detector 70 then passes through the fluid conduit 60 to the waste receptacle 74.

The apparatus for determination of concentrations 91 set forth in FIG. 4 is used in a manner similar to the apparatus for determination of concentrations 10 in FIG. 3. However, the apparatus for the determination of concentrations 91 does not have a reagent reservoir and associated pump and mixer and hence there is no addition of and mixing of a reagent from the reagent reservoir. With this apparatus for determination of concentrations 91 the stirred dilution chamber 78 is connected directly to the optional heating coil via the conduit 45 which is in turn connected as described with respect to the apparatus 10 of FIG. 3. This apparatus for the determination of concentrations 91 is suitable for a sample that needs only a one step addition of chemicals.

The apparatus for determination of concentrations 92 set forth in FIG. 5 is used in a manner similar to the apparatus for determination of concentrations 10 in FIG. 3. However, the sample to be analyzed is subject to digestion prior to being picked up by the sampling valve 16 via the sample probe 20 in a digestion vessel 96 due to microwaves from a microwave source 94 that are directed into the digestion vessel 96. The microwave source 94 is operated under the control of the computer 82 through the electrical conductor 98. It will also be noted that an optional fluid conduit 100 is provided so that reagent from the reservoir 34 can be pumped by the pump 48 through the optional fluid conduit to the fluid conduit 62 so that it enters into the stirred dilution chamber 78 with the sample. This optional fluid conduit 100 is used when an additional reagent is required and the reagent to sample ratio must be constant and at a high value. It will also be noted that the heating coil 66 and the cooling coil 68 are optional for use in this embodiment where heat is required to drive the chemical reaction to improve sensitivity.

The apparatus for determination of concentrations 102 set forth in FIG. 6 is used in a manner similar to the apparatus for determination of concentrations 92 in FIG. 5. However, this embodiment 102 has an additional detector channel 106 that is used for the simultaneous measurement of two different analytes in the same sample. This embodiment 102 is used in basically the same manner as the previously described embodiment 92 except that sampling value 104 is a ten port sampling value capable of transporting allotments or portions of the sample to two reaction flow systems simultaneously. One sample travels from the sampling valve 104 through conduit 62 as described in embodiment 92. For the second sample, reservoirs 107 and 108 are filled with suitable solvent and reagent, respectively. The pumps 109 and 110 are started resulting in the pumping of reagent from the reservoir 107 through conduit 111, through the pump 109 and through the conduit 115 to the sampling valve 104 and the pumping of reagent from reservoir 108 through conduit 112, through the pump 110 and through the conduit 116 to the mixer 114.

From the sampling valve 104, the second sample travels through conduit 120 to the second stirred dilution chamber 118 where the sample is diluted rapidly in the previously indicated manner. This diluted sample then is transferred through conduit 122 to the mixer 114. From the mixer 114 the diluted sample and reagent mixture flows through a conduit 126 to the optional heating coil 124 where a chemical reaction takes place and from the heating coil 124 the fluid passes to an optional cooling coil 128 through the conduit 130. From the cooling coil 128, the mixed and diluted sample goes through the conduit 134 to the detector 132 that monitors the presence and then the absence of the sample under analysis. The computer 82 obtains this information via electrical conductor 138 and uses it to calculate the concentration of the sample being analyzed in the previously indicated manner. Fluid from detector 132 then passes through the conduit 136 to the waste receptacle 74.

The apparatus for determination of concentrations 140 set forth in FIG. 7 is used in substantially the same manner as the embodiment 92 set forth in FIG. 5. However, an additional reagent channel 184 is added to the system which allows additional chemical(s) to be introduced, sequentially, to accomplish the determination of analyte concentrations. This reagent channel 184 is used as follows. Reagent reservoir 186 is filled with an appropriate reagent. Pump 190 is started resulting in the pumping of reagent from reservoir 186 through the fluid conduit 188, through the pump 190 and through the fluid conduit 192 to the mixer 194. From the other mixer 52, the previously mixed sample travels through the fluid conduit 193 to the mixer 194 where it is mixed with new reagent. From the mixer 194, the mixed sample and new reagent travel through conduit 195 to the optional heating coil 66. It will also be noted that an optional fluid conduit 197 and mixer 189 is provided so that reagent from the reservoir 186 can be pumped by the pump 190 through the optional fluid conduit and mixer to the fluid conduit 58 so that it enters the detector 70 with the mixed sample and reagent. This optional fluid conduit 197 and mixer 189 are used when the additional reagent must be added after heating and cooling and immediately prior to detection in the detector 70.

The apparatus for determination of analyte concentrations 141 set forth in FIG. 8 is used in substantially the same manner as the embodiment 92 set forth in FIG. 5. However, an additional detector channel 142 has been added to the system which permits two different analytes to be measured in the same sample when the analytical chemistries are compatible. This second detector channel functions as follows. Reagent reservoir 144 is filled with appropriate reagent. Pump 148 is started resulting in the pumping of reagent from reservoir 144 through the fluid conduit 146, through pump 148, through the fluid conduit 150 to the mixer 152.

From the stirred dilution chamber 78, the sample diluted with sample solvent travels through the conduit 154 to the mixer 152, the mixed sample and reagent travel through the conduit 158 to detector 156 where the presence and absence of sample are detected by the detector 156. Electronic signals from detector 156 are conveyed to computer 82 via conductor 162. The mixed sample and reagent travel from detector 156 through the fluid conduit 160 to the mixer 52 where the sample is mixed with an additional reagent as previously described in connection with the embodiment 92 set forth in FIG. 5.

As illustrated in FIGS. 5, 6, 7, and 8 the continuous flow digester 280 of FIG. 14 can replace the microwave or other energy source 94 and digestion vessel 96. The embodiment of the apparatus for determination of analyte concentration 92 combined with the continuous flow digester 280 is designed to digest samples in a continuous manner in order to release bound analytes prior to analysis. An example of this would be digestion of wastewater containing protein (bound nitrogen) so that total nitrogen could be quantified in the wastewater. In operation, solutions to be digested and analyzed are withdrawn through conduit 285 by pump 296 and pumped to mixer 297 where these solutions are mixed with oxidant and, when necessary, a catalyst. The mixed solutions then flow into Teflon digester coil 286. Microwaves generated by magnetron 282 travel down waveguide 284 where they are absorbed by liquid in the digester coil 286 where the process of digestion takes place. Solutions then go through the coil 290 to optional ultraviolet lamp where additional digestion takes place, through cooling system 294 on to a Tee 295 where samples are removed by the conduit 20 into apparatus for determination of analyte concentrations such as the apparatus 92 of FIG. 5.

Volumes of digested solutions not removed for analysis at Tee 295 travel on to the waste receptacle such as the receptacle 74. Optionally, conduit 298 may be connected directly to sample probe conduit 20, and the entire digested sample directed through sample value 16 or 104. Conduit 285 is connected in an appropriate manner to source of sample solution to be digested (not shown). Pump 296 is then started resulting in pumping of solution through conduit 285, through pump 296, through the conduit 312 and to the mixer 297. The oxidant/catalyst reservoir 281 is filled with a suitable solution. Pump 291 is started resulting in the pumping of oxident/catalyst from the reservoir 281 through the conduit 283 through pump 291 through the conduit 293 to the mixer 297.

From the mixer 297, the mixed solution travels through the conduit 313 and through microwave digester coil 286. Microwaves generated by magnetron 282 travel through the waveguide 284 and interact with mixed solution in the microwave digester coil 286 thereby heating mixed solution and causing digestion of the sample. The magnetron 282 is controlled by the computer 82 via the conductor 287 that is connected to the computer 82. The digested sample travels through the conduit 288 and through the optional ultraviolet lamp coil 290 where ultraviolet energy from optional ultraviolet lamp 292 further digests the sample. The further digested sample travels through conduit 289, through cooling system 294, through conduit 298 to the sampling Tee 295. Upon demand from apparatus for determination of analyte concentration 92, further digested solution travels through conduit 20 to the sampling valve 16 or 104. Other digested sample not directed through the conduit 20 travels through the conduit 299 to the waste receptacle 74.

An optional oxidant/catalyst reservoir pumping is shown as dashed lines in FIG. 14. In operation, reservoir 302 is filled with appropriate solution. Optional pump 304 is started resulting in the pumping of solution from the reservoir 302 through conduit 306, through pump 304, through conduit 308 to mixer 310. From mixer 310, mixed solutions flow through conduit 293 to the mixer 297.

The operation of the continuous flow digester 280, in connection with the apparatus for determination of concentrations 102, 140, and 142 of the respective FIGS. 6, 7, and 8 is similar to that previously described with respect to the apparatus for the determination of concentrations of FIG. 5. As indicated previously, the distribution valve system 300 can be used at the entrance to the sampling side of the sampling valve 16 or 104 in the apparatus previously described that is set forth in FIGS. 3 through 8. When in use the distribution valve 301 is connected to the sample probe 20. The valve 301 permits the connection of one of a plurality of sample input conduits 303, 307, 309, and 311 to the sample probe 20. Also, a normal sample in fluid conduit 317 can be introduced by connecting it to the conduit 311 by activation of the stream selection valve 305 which would normally connect conduit 316 to the conduit 311.

A summary of the general procedures for measuring samples containing wide ranging concentrations of analytes using the previously described apparatus for determination of concentrations 10, 92, 102, 140, and 141 set forth in FIGS. 3 through 14 is set forth below:

Preliminary

1. Ascertain that the apparatus or instrument is set up correctly for the analysis to be conducted.
2. Determine that the concentration of standards encompass the expected concentration of samples.
3. Ascertain that carrier and reagents have not expired.

Procedure

1. Start instrument.
2. Check to ensure that all components of the instrument are functioning properly.
3. Set the pumps to an appropriate flow rate for carrier and reagents.
4. Establish a valid detector baseline (either a straight line on a recorder or stable colorimeter output voltage).
5. Inject standards, one at a time, into instrument. Standards of at least three different concentrations should be employed and at least one sample of each standard should be injected.
6. Record peak width or measure peak width about 0.1 volt above baseline.
7. Plot a standard curve using peak width versus logarithm concentration of standards. Calculate the correlation coefficient of a linear least squares regression. If the correlation coefficient is equal to or greater than the value giving an acceptable error, proceed. If above criteria are not met, thoroughly check instrument, reagents, standards and then reanalyze the standards.
8. Inject samples of unknowns into instrument. Record or measure peak width as indicated above.
9. Revalidate standards periodically (about every 20 samples) while analyzing samples of unknowns by analyzing the second of 3 standards and comparing the calculated value to the known value. If the values agree within a preset acceptable percent of error, then continue to analyze unknown samples. If the calculated value is outside acceptable error, restandardize the instrument as described above.
10. Calculate concentrations of unknown samples from a standard plot (logarithm of concentration of standards versus peak width) or calculate concentration from the following equation:

$$C = Antilogarithm[(y-a)/b]$$

Where
  y = peak width of sample,
  a = intercept from solution of linear regression of appropriate standards,
  b = slope from solution of linear regression of appropriate standards,
  c = concentration of the sample injected and being analyzed.

11. After completion of analysis, shut down the instrument according to the standard procedures.

In view of the foregoing it is apparent that the method of the invention includes the following. Determining the concentration of a substance in a sample including the steps of: providing a sample volume containing an unknown amount of a substance, providing a constant volume of carrier fluid, providing the correct proportions of reagent(s) to measure the analyte substance, providing a detector for detecting the presence of the substance, injecting the sample into the volume of carrier fluid, continuously diluting the sample in a stirred dilution chamber, detecting the initial presence of the substance in the carrier fluid through the use of the detector, detecting the subsequent lack of presence of the substance in the carrier fluid through the use of the detector, and determining the elapsed time from the detection of the initial presence of the substance through the use of the detector and the detection of the subsequent lack of presence of the substance through the use of the detector.

The elapsed time is then used to calculate the concentration of unknown samples by the following equation:

$$C = Antilogarithm[(y-a)/b]$$

Where
  y = peak width of sample,
  a = intercept from solution of linear regression of appropriate standards,
  b = slope from solution of linear regression of appropriate standards,
  c = concentration of the sample injected and being analyzed.

This calculation can be done manually or it can be done through the use of the computer 82. In the preferred embodiment of the method the elapsed time is determined by optically detecting the presence of an analyte substance in the flow cell detector after it passes through the stirred dilution chamber and when the analog substance signal is above a preset voltage (trigger level) from the baseline, a timer is started. The analog signal will quickly reach a maximum and then begin to decrease as the sample concentration in the flow cell detector decreases. The decrease in signal will generally follow an exponential mathematical function as a result of the continuous dilution in the stirred dilution chamber. Once the analog signal falls below the trigger level, the timer is stopped and the elapsed time recorded as the peak width.

The detection of the analyte, or substance whose concentration is to be determined, in the flow cell may require that it be chemically linked to another molecule in order to optically monitor its presence and relative changes in concentration. The simplest case is where the reagent is part of the sample solvent as shown in FIG. 4. A more complex case is where more than one reagent must be added in order to meet the requirements of the chemical reaction. The first case is to simply add a second reagent at any point in the reaction flow system as seen in FIGS. 3 and 5. Consequently, the method of the invention includes providing a substance to chemically react with the substance whose concentration is to be determined and mixing the substances to cause a chemical reaction prior to the step of detecting the initial presence of the substance whose concentration is to be determined in the carrier fluid through the use of the detector in the first case and providing a second substance to chemically react with the substance whose concentration is to be determined and mixing the second substance and the substance whose concentration is to be determined to cause a second chemical reaction, prior to the step of detecting the initial presence of the substance whose concentration is to be determined in the carrier fluid through the use of the detector. The more specific requirements with this method are as follows:

1) The sample/reagent ratio must remain high to optimize the reaction rate. This is accomplished by adding the second reagent prior to the stirred dilution chamber as illustrated in FIG. 5.
2) The second reagent needs to be added after the first reagent has reacted with the analyte sample whose concentration is to be determined. This is accomplished by adding the reagent to the reaction flow stream after the stirred dilution chamber but prior to the detector as illustrated in FIG. 7; and
3) A third or fourth reagent can be added as required.

A multiplicity of analytes may be simultaneously analyzed in the system. Two specific configurations of the apparatus can be used. In the first configuration a ten port valve is used to inject allotments of the same sample into two separate reaction flow pathways as illustrated in FIG. 6. A single sample solvent may be used if the chemistry of the two analytes permits or two separate sample solvents and pathways may be required if the chemistry requirements are incompatible. In either case both flowing reaction systems must have separate stirred dilution chambers. The addition (if required) of a second reagent can be accomplished as in either of the two methods above. In the second configuration, a single six port valve will inject single samples into a single reaction flow system with a single stirred dilution. The first analyte is measured as above and when the sample leaves the first detector another reagent is added, specific for the second analyte, using the above methods and then enters a second detector where the peak width of the second analyte is measured as illustrated in FIG. 8. A second detector is not required if a single detector can distinguish two different colored substances at the same time (such as a diode array or a multiple wavelength detector).

A sample with a substance whose concentration is to be determined, may require some pretreatment such as digestion prior to analysis. The apparatus of this invention will present the sample for analysis after digestion such as in FIG. 14 and any of the above scenarios may be followed. Consequently, in this case the method includes the step of providing means to digest the sample and the step of digesting the sample prior to injecting the sample into the carrier fluid. The digestion means can include the non-continuous means for digestion of a sample 93 such as that set forth in FIG. 5 or the continuous flow digestion means for digestion of the sample comprising the continuous flow digester 280 of FIG. 14. Consequently, the digestion process step in the method is respectively non-continuous and continuous.

The apparatus for determination of concentrations such as those designated by the numbers 10 and 92 have been used in the following chemical analyses to provide highly accurate results as indicated in the following examples. Examples 1 and 2 are examples of the instrument or apparatus of the invention without the digestion of samples, while examples 3 and 4 used microwave digestion of the samples prior to analysis.

EXAMPLE 1

The following measurements were made using the flow injection device with a 0.3 milliliter volume dilution chamber. A flow rate of 2.5 milliliter per minute of $5 \times 10^{-}M$ phosphate, pH 4.5 buffer containing 0.0008% Bromcresol Green indicator was established as the sample solvent containing reagent. Once the pump was running smoothly, a valid baseline (either a straight line on the recorder or stable colorimeter output voltage) was obtained at 1.5 volts. The sample loop held approximately 20 microliters. The colorimeter trigger was set at 2.1 volts and monitored at about 600 nanometers.

Samples of 0.005N, 0.05N and 0.5N sodium hydroxide were injected into the instrument and the peak width was measured. These widths were 12.6, 44.9 and 73 seconds, respectively. The logarithm of the concentration of the samples versus peak width was plotted and a straight line was obtained. An unknown sample was then injected and the concentration of the unknown sample was then determined by the following equation:

$$C = Antilogarithm[(y-a)/b]$$

Where
y = peak width of sample,
a = intercept from solution of linear regression of appropriate standards,
b = slope from solution of linear regression of appropriate standards,
C = concentration of the sample injected and being analyzed.

This injected sample produced a width of 45.1 seconds for a computed concentration of 0.05N NaOH.

EXAMPLE 2

The following measurements were made using the flow injection device with a 0.3 milliliter volume dilution chamber, two detectors and two sample pumps. A flow rate of 2.5 milliliters per minute of distilled water. Sample solvent (0.01M potassium permanganate in 0.001N sodium hydroxide) was added at the rate of 1 milliter per minute. Reagent (0.001M phenolphthalein in 0.05M borate buffer, pH 8) also was added at 1 milliter per minute. Once the pumps were running smoothly, valid baselines (either a straight line on the recorder or stable colorimeter output voltage) was obtained, the sample loop which held approximately 20 microliters introduced the sample. The colorimeters were recording at about 540 nanometers.

Samples of 2, 3.33, 5 and 10 parts per million borohydride at pH 7 were injected into the instrument and the peak width was measured. These widths were 8.5–9.0, 14.5–15.0, 19.0–19.5 and 23.0–23.5 seconds, respectively. No signal was observed at detector 2. The logarithm of the concentration of the samples versus peak width was plotted and a straight line was obtained. An unknown sample at pH 13 was then injected and the concentration of the unknown borohydride sample was determined by the following equation using data from detector 1. Detector 2 produced a peak having a width of 18.5 seconds.

$$C = Antilogarithm[(y-a)/b]$$

Where y, a, b, and C are the same as defined in Example 1. Such a sample was injected and it produced a width of 14.5 seconds for a concentration of 5 parts per million of borohydride.

EXAMPLE 3

For determination of Kjeldahl nitrogen, a sample of ammonium sulphate was digested.

The following measurements were made using the flow injection device with a 0.3 milliliter volume dilution chamber, two pumps, one detector, and heating and cooling coil. Sample solvent containing reagent 1 (20.8 grams tetra sodium EDTA dihydrate, 9.52 milliliters phenol and 250 milligram sodium nitroprusside diluted to 1 liter with deionized water) was pumped at 1 milliliter per minute simultaneously with Reagent 1 (31.8 grams $Na_3PO_4 \cdot 12H_2O$, 7.1 grams $Na_2HPO_4 \cdot 12H_2O$, 11.4 grams NaOH and 8.4 milliliters chlorox diluted to 1 liter with deionized water) also at 1 milliliter per minute which was added immediately prior to the heater. Once the pumps were running smoothly, a valid baseline (either a straight line on the recorder or stable colorimeter output voltage) was obtained, the sample loop which held approximately 20 microliters introduced the sample. The colorimeter was recording at 660 nanometers.

Samples of digest containing 5, 50 and 500 micrograms per milliliter were injected into the instrument and the peak width was measured. These widths were 17.8, 38.7 and 61.7 seconds, respectively. The logarithm of the concentration of the samples versus peak width was plotted and a straight line was obtained. An unknown sample was then injected and the concentration of the unknown sample was determined by the following equation:

$$C = Antilogarithm[(y-a)/b]$$

Where y, a, b, and C are defined as set forth in Example 1. The injected sample produced a width of 39 seconds for a computed concentration of 8% protein.

EXAMPLE 4

The following measurements were made using the flow injection device with a 0.3 milliliter volume dilution chamber, two pumps one detector, a heating coil and cooling coil. Sample solvent containing reagent (9.52 milliliters phenol and 250 milligrams sodium nitroprusside diluted to 1 liter with deionized water) was pumped at 1 milliliter per minute simultaneously with Reagent 1 (31.8 grams $Na_3PO_4 \cdot 12H_2O$, 7.1 grams $Na_2HPO_4 \cdot 12H_2O$, 11.4 grams NaOH and 8.4 milliliters chlorox diluted to 1 liter with deionized water) also at 1 milliliter per minute which was added immediately prior to the heater. Once the pumps were running smoothly, a valid baseline (either a straight line on the recorder or stable colorimeter output voltage) was obtained, the sample loop which held approximately 20 microliters introduced the sample. The colorimeter was recording at 660 nanometers. Samples of 5, 50, and 200 micrograms per milliliter were injected into the instrument and the peak width was measured. These widths were 12.7, 18.5 and 27.2 seconds, respectively. The logarithm of the concentration of the samples versus peak width was plotted and a straight line was obtained. An unknown sample was then injected and the concentration of the unknown sample was determined by the following equation:

$$C = Antilogarithm[(y-a)/b]$$

Where y, a, b, and c are the same as defined in Example 1. The injected sample produced a width of 19.0 seconds for a concentration of 8% protein.

Based upon Examples 3 and 4, it can be seen that the accuracy of the analysis is 1.4 to 3.5 times greater with ethylenediaminetetraacetic acid (EDTA) than without EDTA.

Although the apparatus for determination of concentrations 10, 91, 92, 102, 140, and 141 have been described in terms of a flow detector 70 in the preferred embodiment, the invention can include other types of detectors such as fluorimeter, luminometer, infrared, FTIR, and nuclear radiation detectors. The choice of a particular type of detector will depend upon the type of analyte or its derivative that is to be detected and whether it is colored, fluorescent, luminescent, passes a measureable band of light in the infrared, visible or ultraviolet spectrum or emits alpha, beta, or gamma radiation or neutrons.

The apparatus for the determination of concentrations 10, 91, 92, 102, 140, and 141 have been described in terms of a flow injection analysis type system for determination of the concentration of an analyte. However, the apparatus for determination of concentrations 10, 91, 92, 102, 140, and 141 can also be used in other systems such as in a pollution control system where it would detect pollutants or gasses in a liquid or gas stream that exceeded permissible concentrations.

Although the invention has been described in considerable detail with reference to certain preferred embodiments, it will be appreciated and understood that variations and modifications can be made to the invention without departing from the spirit and scope of the invention as defined in the appended claims.

What is claimed is:

1. A method for determining the concentration of a substance in a sample comprising the steps of:
   a. providing a sample containing an unknown amount of a substance,
   b. providing a volume of carrier fluid,
   c. providing a stirred dilution chamber with a magnet located therein,
   d. providing an electromagnetic coil located adjacent said stirred dilution chamber, e. providing an electromagnetic coil activating circuit connected to said electromagnetic coil for providing electronic pulses to said coil,
f. providing a detector for detecting the presence of said substance,
g. activating said electromagnetic coil activating circuit to provide electronic pulses to said coil to activate coil to cause stirring of the magnet in said stirred dilution chamber,
h. diluting said sample in a volume of carrier fluid in said stirred dilution chamber,
i. detecting the initial presence of said substance in said carrier fluid through the use of said detector,
j. detecting the subsequent lack of presence of said substance in said carrier fluid through the use of said detector, and
k. determining the elapsed time form said detection of the initial presence of said substance through the use of said detector and said detection of the subsequent lack of presence of said substance through the use of said detector to determine the concentration of the substance in said sample.

2. The method for determining the concentration of a substance in a sample of claim 1 wherein the step of injecting said sample into said volume of carrier fluid is accomplished in such a manner that there is a very rapid rise in the presence of the substance in said carrier fluid.

3. The method for determining the concentration of a substance in a sample of claim 1 further comprising the steps of providing mean for digesting said sample and the step of digesting said sample though the use of said digesting means prior to the step of diluting said sample in a volume of carrier fluid in said stirred dilution chamber.

4. The method for determining the concentration of a substance in a sample of claim 1 further comprising the steps of providing a volume of a substance capable of chemically reacting with the substance in said sample and the step of mixing said chemically reactive substances with said sample prior to the step of detecting the initial presence of said substance in said carrier fluid through the use of said detector.

5. The method for determining the concentration of a substance in a sample of claim 4 further comprising the steps of providing a volume of a second substance capable of chemically reacting with the substance in said sample and the step of mixing said second chemically reactive substance with said sample prior to the step of detecting the initial presence of said substance in said carrier fluid through the use of said detector.

6. The method for determining the concentration of a substance in a sample of claim 5 further comprising the steps of providing a second sample containing an unknown amount of a second substance, the step of injecting said second sample into a volume of carrier fluid and the step of detecting the presence of said second substance in said carrier fluid through the use of said detector.

7. Apparatus for the determination of concentrations of a substance comprising: a sample flow system; a reaction flow system for reacting with samples form said sample flow system; means for introducing samples form said sample flow system into said reaction flow system; and means for rapidly diluting the substance whose concentration is to be determined, said means of rapidly diluting the substance whose concentration is to be determined comprising a stirred dilution chamber having a magnet located therein, an electromagnetic coil located adjacent to said stirred dilution chamber and an electromagnetic coil activating circuit connected to said electromagnetic coil for providing electronic pulses to activate said electromagnetic coil; and a detector operatively connected to said means for rapidly diluting the substance whose concentration is to be determined.

8. The apparatus for the determination of concentration of a substance of claim 7 further comprising an additional reaction flow system operatively associated with said stirred dilution chamber.

9. The apparatus for the determination of concentrations of a substance of claim 8 further comprising a second detector operatively associated with said additional reaction flow system.

* * * * *